US010006901B2

(12) United States Patent
Schuler et al.

(10) Patent No.: US 10,006,901 B2
(45) Date of Patent: Jun. 26, 2018

(54) CD4+CD25+ REGULATORY T CELLS FROM HUMAN BLOOD

(75) Inventors: Gerold Schuler, Spardorf (DE); Detlef Dieckmann, Uttenreuth (DE)

(73) Assignee: ARGOS THERAPEUTICS, INC., Durham, NC (US)

( * ) Notice: Subject to any disclaimer, the term of this patent is extended or adjusted under 35 U.S.C. 154(b) by 0 days. days.

(21) Appl. No.: 13/530,488

(22) Filed: Jun. 22, 2012

(65) Prior Publication Data

US 2012/0328563 A1 Dec. 27, 2012

Related U.S. Application Data

(63) Continuation of application No. 10/661,804, filed on Sep. 12, 2003, now abandoned, which is a continuation of application No. PCT/EP02/02671, filed on Mar. 12, 2002.

(30) Foreign Application Priority Data

Mar. 12, 2001 (EP) ..................................... 01106033

(51) Int. Cl.
  A01N 63/00 (2006.01)
  G01N 33/50 (2006.01)
  A61K 35/17 (2015.01)
  C12N 5/0783 (2010.01)

(52) U.S. Cl.
  CPC ......... *G01N 33/5002* (2013.01); *A61K 35/17* (2013.01); *C12N 5/0636* (2013.01); *G01N 33/505* (2013.01); *C12N 2500/14* (2013.01); *C12N 2501/01* (2013.01); *C12N 2501/23* (2013.01); *C12N 2501/51* (2013.01); *C12N 2501/515* (2013.01)

(58) Field of Classification Search
  None
  See application file for complete search history.

(56) References Cited

U.S. PATENT DOCUMENTS

| | | | |
|---|---|---|---|
| 5,721,910 A | 2/1998 | Unger et al. | |
| 5,752,020 A | 5/1998 | Ando | |
| 5,950,214 A | 9/1999 | Rivette et al. | |
| 5,991,751 A | 11/1999 | Rivette et al. | |
| 5,991,780 A | 11/1999 | Rivette et al. | |
| 5,999,907 A | 12/1999 | Donner | |
| 6,014,663 A | 1/2000 | Rivette et al. | |
| 6,038,561 A | 3/2000 | Snyder et al. | |
| 6,358,506 B1 * | 3/2002 | Horwitz | 424/85.2 |
| 6,534,055 B1 | 3/2003 | June et al. | |
| 6,670,146 B2 * | 12/2003 | Barrat et al. | 435/41 |
| 6,803,036 B1 | 10/2004 | Horowitz | |
| 7,479,269 B2 | 1/2009 | June et al. | |
| 2001/0003746 A1 | 6/2001 | Sodemann | |
| 2001/0003950 A1 | 6/2001 | Zhang et al. | |
| 2002/0090357 A1 | 7/2002 | Barrat et al. | |
| 2002/0182730 A1 * | 12/2002 | Gruenberg | 435/375 |
| 2003/0005085 A1 | 1/2003 | Matsuno | |
| 2003/0013540 A1 | 1/2003 | Penrose | |
| 2003/0014491 A1 | 1/2003 | Horvitz et al. | |

FOREIGN PATENT DOCUMENTS

| | | |
|---|---|---|
| EP | 0 380 362 | 8/1990 |
| EP | 1 409 650 | 4/2006 |
| EP | 1379625 B1 | 6/2010 |
| WO | 91 00345 | 1/1991 |
| WO | 92 11348 | 7/1992 |
| WO | 93 02108 A | 2/1993 |
| WO | 95 07991 | 3/1995 |
| WO | 96 09396 | 3/1996 |
| WO | 98 56417 A | 12/1998 |
| WO | 00 42856 | 7/2000 |
| WO | WO 0042856 A1 * | 7/2000 |
| WO | 02 097070 | 12/2002 |

OTHER PUBLICATIONS

Taylor et al. 2011, J. Transplant. pp. 1-7.*
Elrefaei et al., 2010, AIDS res. and human retro. vol. 26: 329-337.*
Takahashi et al., 1998, Int. Immunol. vol. 10: 1969-80.*
Horwitz et al., 2003, vol. 74: 471-78.*
Vieira et al., 2004, J. Immunol. vol. 172: 5986-93.*
Jonuleit et al., 2003, J. Immunol. vol. 171: 6323-27.*
Nanki et al., 2000, J. Immunol. vol. 164: 5010-5014.*
Takahashi et al., 2000, J. Exp. Med. vol. 192: 303-309.*
Linsley et al., 1996, Immunity, vol. 4: 535-543.*
Metz et al., 1998, J. Immunol. vol. 161: 5855-5861.*
Oppostion filed by Miltenyl Biotech GmbH against EP 1 379 625 on Mar. 30, 2011, in German language.
English translation of Miltenyl Opposition filed Mar. 30, 2011.
Groux et al, 1997, Nature, vol. 389: 737-742.
Levings M., et al., J. Exp. Med., 1993: 1295-1301 (2001).
Fujimaki, W. et al., Clin. Develop. Immunol., 2008: 1-12 (2008).
Ng, W. et al., BSI Congress 2000, vol. 101, Supplement 1, Abstract 3.12 (2000).
Taams, L. et al., BSI Congress 2000, vol. 101, Supplement 1, Abstract IS6 (2000).
Ng, W. et al, Blood, 98: 2736-2744 (2001).
Taams, L. et al., Eur. J. Immunol., 31: 1122-1131 (2001).
Read, S. et al., J. Exp. Med., 192: 295-302 (2000).
Olivares-Villagomez, D. et al., J. Immunol., 164: 5499-5507 (2000).
Sakaguchi, S., Cell, 101: 455-458 (2000).
Stephens, L. et al., Eur. J. Immunol., 31: 1247-1254 (2001).
Nagahama, K. et al., Methods Molecul. Biol,. 380: 431-442 (2007).
Takahata et al., 2004, Exp. Hem. vol. 32: 622-629.
Levings et al., May 2001, J. Immunol. vol. 166: 5530-5539.
Dieckmann et al., Jul. 2002, Journal of Experimental Medicine, vol. 196, No. 2: 247-253.
Taylor et al., 2005, "T regulatory cells and allergy", Microbes and Infection, 7: 1049-1055.

(Continued)

*Primary Examiner* — Amy E Juedes
(74) *Attorney, Agent, or Firm* — Norris McLaughlin & Marcus, P.A.

(57) ABSTRACT

The present invention provides suppressive and/or regulative human CD4+CD25+ T cells, a method for expanding same, and the use of the suppressive and/or regulative human CD4+CD25+ T cells and the expanded T cells as regulatory agent.

10 Claims, 13 Drawing Sheets

(56) References Cited

OTHER PUBLICATIONS

Thornton et al., 1998, The Journal of Exp. Med. 188: 287-296.
Huang Z., Jun. 2000, Pharmacol. Ther., Jun. 2000, 86 (3): 201-15.
Metzler et al., Jul. 1997, Nat. Struct. Biol., 4(7): 527-31.
Brode et al., Apr. 8, 1991, Journal of Cellular Biochemistry, vol. 15, Part G., p. 205.
Nakamura et al., 2001 J. Exp. Med. vol. 194: 629-644.
Jonuleit et al., Jul. 15, 2002, J. Exp. Med., vol. 196: 255-260.
Baecher-Allan et al., 2001, J. Immunol., vol. 167: 1245-1253.
Office Action dated Apr. 20, 2006 by Examiner for corresponding U.S. Appl. No. 10/618,134.
Office Action dated Dec. 21, 2006 by Examiner for corresponding U.S. Appl. No. 10/618,134.
Office Action dated Aug. 7, 2007 by Examiner for corresponding U.S. Appl. No. 10/618,134.
Office Action dated Jul. 1, 2008 by Examiner for corresponding U.S. Appl. No. 10/618,134.
Office Action dated Mar. 16, 2009 by Examiner for corresponding U.S. Appl. No. 10/618,134.
Office Action dated Sep. 3, 2008 by Examiner for corresponding U.S. Appl. No. 11/765,720.
Office Action dated May 26, 2009 by Examiner for corresponding U.S. Appl. No. 11/765,720.
Thornton et al, Journal of Immunology, 2000, 164: 183-190.
Rohowsky-Kochan et al, Multiple Sclerosis (2000) 6, 69-77.
Office Action dated Oct. 25, 2010 in corresponding U.S. Appl. No. 10/618,134.
Office Action dated Oct. 27, 2010 in corresponding U.S. Appl. No. 11/765,720.
Chen et al. (2003) J. Exp. Med. 198: 1875-1886, "Conversion of Peripheral CD4+CD25—Naïve T Cells to CD4+CD25+ Regulatory T Cells by TGF-β Induction of Transcription Factor Foxp3".
Lechler et al. (2001) Phil. Trans. R. Soc. Lond. 356: 625-637, "T-cell anergy and peripheral T-cell tolerance".
Office Action dated Feb. 3, 2010 by Examiner for U.S. Appl. No. 10/618,134.
Office Action dated Mar. 16, 2010 by Examiner for U.S. Appl.. No. 10/618,134.
Office Action dated Dec. 15, 2009 by Examiner for U.S. Appl. No. 11/765,720.
Office Action dated Mar. 16, 2010 by Examiner for U.S. Appl. No. 11/765,720.
Javier Mestas and Christopher C.W. Hughes; J. Immunol 2004; 172; 2731-2738.
Leung et al., J. Biol. Chem. vol. 270: 25107-25114, 1995.
Jago et al., 2004, Clin. Exp. Immunol. vol. 136: 463-471.
Stout et al., J. Immunol. vol. 150: 5330-5337 (1993).
Miltenyi product information, CD25 microbeads, pp. 1-3; (2007).
Koulis et al., Allergy Clin immunol. vol. 107, pp. S294-S295 (Feb. 2001).
Thornton et al., J. Exp. Med. vol. 188, p. 287-296 (1998).
De Jong et al., International Immunology, vol. 6, No. 4, pp. 631-638, (Jan. 1994).
Jonuleit et al., J. Exp. Med. vol. 192, No. 9, pp. 1213-1222 (Nov. 6, 2000).
Shimizu et al., J. Immunol., vol. 163, No. 10, pp. 5211-5218 (1999).
Alberts et al., eds., "Molecular Biology of the Cell," 3rd edition (1994), pp. 142, 157, 158, 748,749, and 853 (Garland Publishing, Inc., New York, NY, USA).
Battaglia et al., "Rapamycin selectively expands CD4+ CD25+ FoxP3+ regulatory T cells," Blood, 2005, pp. 4743-4748, vol. 105.
DeVries et al., Frequency of circulating Tregs with demethylated FoxP3 intron 1 in melanoma patients receiving tumor vaccines and potentially Treg-depleting agents, Clin. Cancer Res., 2010, pp. 841-848, vol. 17.
Ferlin et al., "Present difficulties and future promise of MHC multimers in autoimmune exploration," Curr. Op. Immunol., 2000, pp. 670-675, vol. 12.
Goldsby et al., eds., "Kuby Immunology," 4th edition (2000), pp. 203-206 and 513 (W.H. Freeman and Co., New York, NY).
Haskins et al., "The major histocompatibility complex-restricted antigen receptor on T cells: I. Isolation with a monoclonal antibody," J. Exp. Med., 1983, pp. 1149-1169, vol. 157.
Jacobs et al., "Dendritic cell vaccination in combination with anti-CD25 monoclonal antibody treatment: a phase I/II study in metastatic melanoma patients," Clin. Cancer Res., 2010, pp. 5067-5078, vol. 16.
Miyara and Sakaguchi, "Human FoxP3+ CD4+ regulatory T cells: their knowns and unknowns," Immunol. Cell Biol., 2011, pp. 346-351, vol. 89.
Milteny Biotec, Inc., "Treg expansion kit," 2010, datasheet published by Miltenyi Biotec, pp. 1-3.
Ribas et al., "Genetic immunotherapy for cancer," The Oncologist, 2000, pp. 87-98, vol. 5.
Taga et al., "Preferential expression of IL-2 receptor subunits on memory populations within CD4+ and CD8+ T cells," Immunology, 1991, pp. 15-19, vol. 72.
Takahashi et al., "Immunologic self-tolerance maintained by CD25+ CD4+ naturally anergic and suppressive T cells: induction of autoimmune disease by breaking their anergic/suppressive state," Int'l. Immunol., 1998, pp. 1969-1980, vol. 10.
Office Action dated Jul. 20, 2011, for copending U.S. Appl. No. 10/618,134, filed Jul. 11, 2003.
Notice of Allowance dated Aug. 5, 2011, for U.S. Appl. No. 11/765,720, filed Jun. 20, 2007.
Takahashi et al., J. Exp. Med., vol. 192, No. 2, pp. 303-309 (Jul. 17, 2000).
Horwitz et al., Arthritis Res. 4: 241-246 (2002).
Taylor et al., Immunology and Cell Biology, 79: 358-367 (2001).
Bacchetta et al., J. Exp. Med. 179: 493-502 (1994).
Cottrez et al., Transplantation, 77: S12-S16 (2004).
Dieckmann et al., J. Exp. Med., 193: 1303-1310 (Jun. 4, 2001).
Jackson et al., Clin. Immunol. Immunopathol 54(1): 126-133 (1990).
Kanegane et al., Int. Immunol, 3(12): 1349-56 (1991).
Rohowsky-Kochan et al., Multiple Sclerosis 6: 69-77 (2000).
Thorton et al., J. Immunol, 164: 183-190 (2000).
Office Action issued by Examiner for U.S. Appl. No. 10/618,134, dated Oct. 15, 2010.
Mason, Don, "T-cell-mediated control of autoimmunity"; Arthritis Res 2001; 3:133-135.
F. Powrie, "Regulatory T Cells in the control of inflammatory bowel disease"; Abstracts, Diabetes/Metabolism Research and Reviews; vol. 17, Suppl 1; Jan.-Feb. 2001.
Sakaguchi, Shimon et al; "Immunologic Self-Tolerance Maintained by Activated T Cells Expressing 11-2 Receptor a-Chains (CD25)"; The Journal of Immunology; vol. 155, Issue 3, 1995; 1151-64.
Tang et al"CD4+ Foxp3+ regulatory T cell therapy in transplantation"; Journal of Molecular Cell Biology (2012) 4, 11-21.
Tu, et al; "Efficient generation of uman alloantigen-specific CD4 regulatory T cells from naive precursors by CD40– activated B cells"; Blood, Sep. 15, 2008, vol. 112, No. 6, 2554-2562.
Yamagiwa, et al; "A role for TGF-β in the Generation and Expansion of CD4+ CD25+ Regulatory T Cells from Human Peripheral Blood"; The Journal of Immunology, 2001, 166; pp. 728.
Schevach, et al; "The Critical Contribution of TGF-β to the Induction of Foxp3 Expression and Treg Function"; Eur. J. Immuno., Apr. 2008; 38 (4); pp. 915-917.

\* cited by examiner

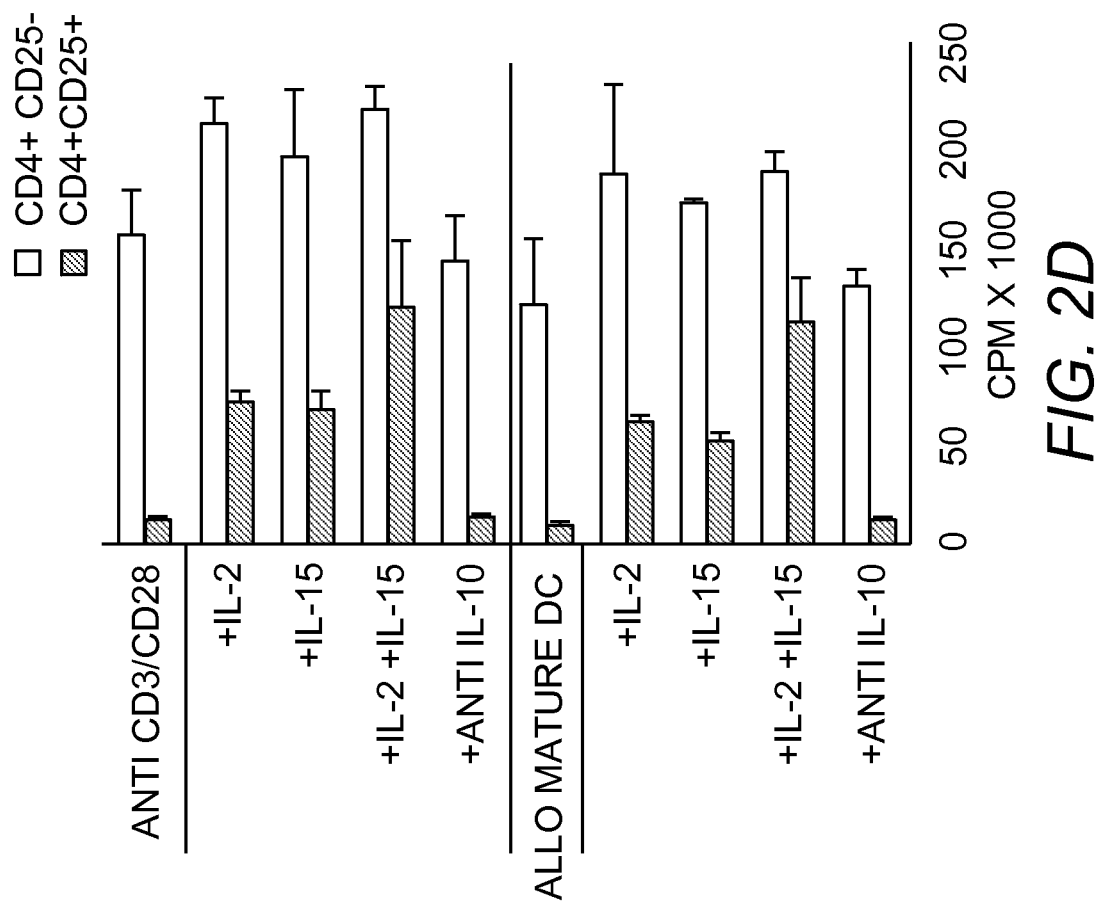

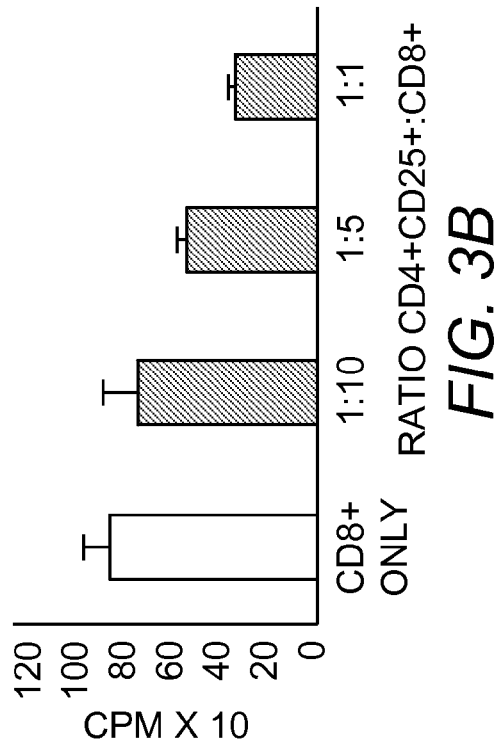
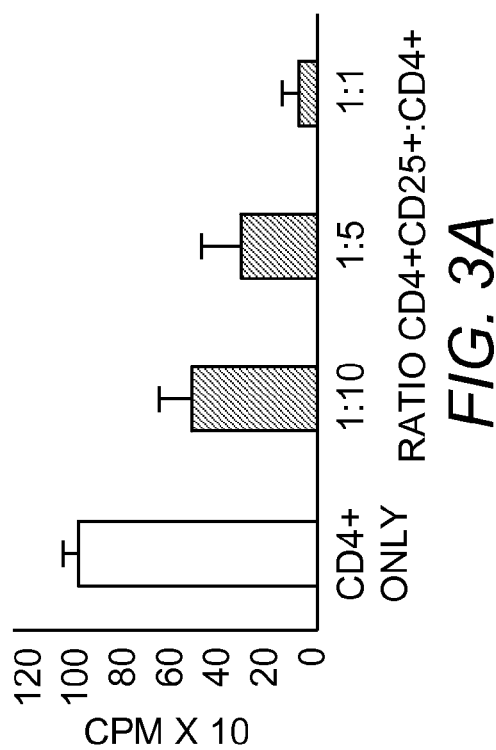
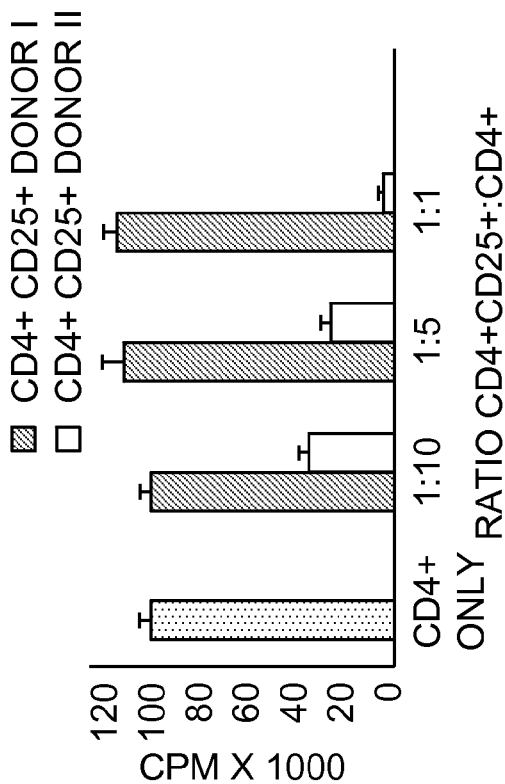

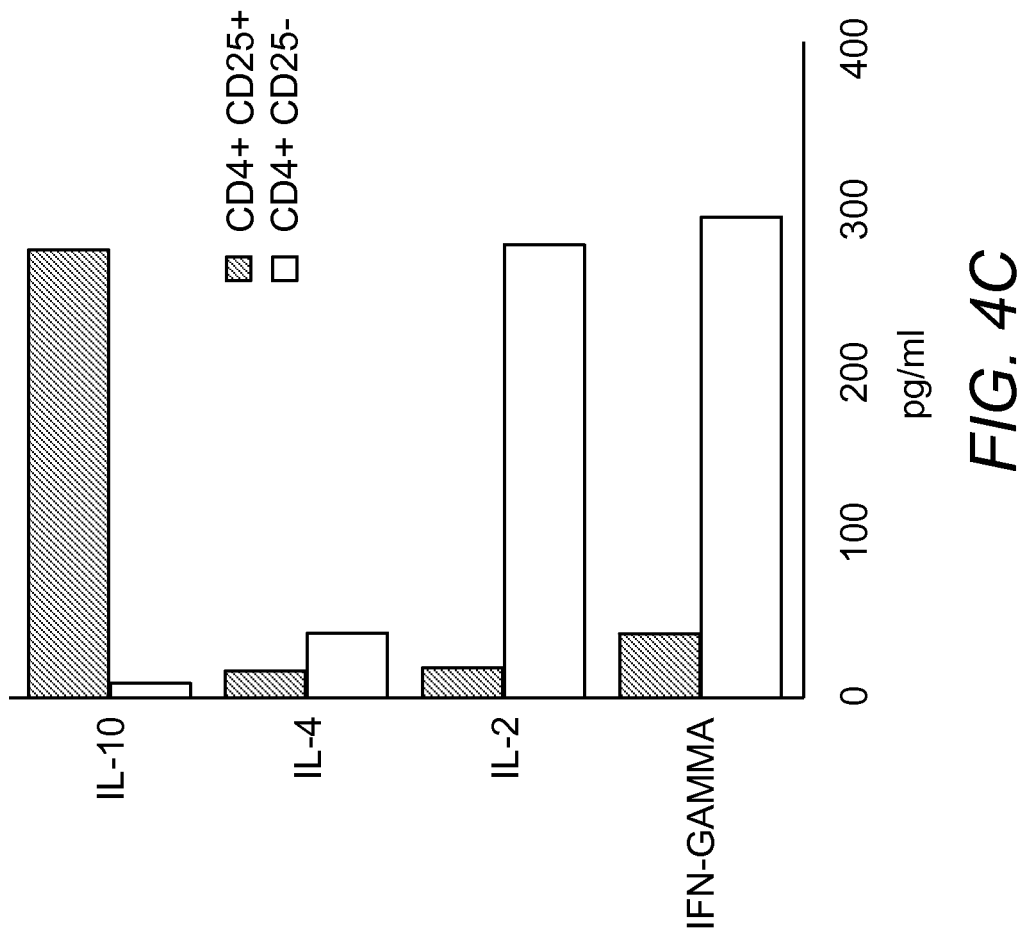

CD4+CD25+ REGULATORY T CELLS FROM HUMAN BLOOD

This application is a continuation of U.S. patent application Ser. No. 10/661,804, filed Sep. 12, 2003, now pending, which is, in turn, a continuation of PCT/EP02/02671, filed Mar. 12, 2002, which, in turn, claims priority of European Patent Application No. 01106033.2, filed Mar. 12, 2001, the entire contents of which three patent applications is incorporated herein by reference.

The present invention provides suppressive and/or regulative human CD4+CD25+ T cells, a method for expanding same, and the use of the suppressive and/or regulative human CD4+CD25+ T cells and of the corresponding expanded T cells as regulatory agent.

BACKGROUND OF THE INVENTION

Immunological self-tolerance is critical for the prevention of autoimmunity and maintenance of immune homeostasis. The ability of the immune system to discriminate between self and non-self is controlled by mechanisms of central and peripheral tolerance. Central tolerance involves deletion of self-reactive T lymphocytes in the thymus at an early stage of development (Rocha, B. and von Boehmer, H., Science 251:1225-1228 (1991); Kisielow, P. et al., Nature 333:742-746 (1988)). Several mechanisms of peripheral tolerance have been described, including T cell anergy and ignorance (Rocha, B. and von Boehmer, H., Science 251:1225-1228 (1991); Kisielow, P. et al., Nature, 333:742-746 (1988); Schwartz, R. H., Science 248:1349-1356 (1990); Miller, J. F. A. P. and Heath, W. R., Immunol. Rev. 133:131-150 (1993)). Studies ongoing for more than a decade in rodents have provided firm evidence for the existence of a unique CD4+ CD25+ population of "professional" regulatory/suppressor T cells that actively and dominantly prevent both the activation as well as the effector function of autoreactive T cells that have escaped other mechanisms of tolerance (Sakaguchi, S. et al., J. Immunol. 155:1151-1164 (1995); Takahashi, T. et al., Int. Immunol. 10:1969-1980 (1998); Itoh, M. et al., J. Immunol. 162:5317-5326 (1999)). The elimination or inactivation of these cells resulted in severe autoimmune disease, and was also found to enhance immune responses to alloantigens and even tumors (Sakaguchi, S. et al., J. Immunol. 155:1151-1164 (1995); Itoh, M. et al., J. Immunol. 162:5317-5326 (1999); Shimizu, J. et al., J. Immunol. 163: 5211-5218 (1999)). Recent studies revealed that the CD4+ CD25+ regulatory T cells constitute a rather homogenous population (Thornton, A. M., Shevach, E. M., J. Immunol. 164:183-190 (2000)), are derived from the thymus (Itoh, M. et al., J. Immunol. 162:5317-5326 (1999)), are naturally non-proliferative (i.e. anergic) to stimulation via the TCR, but require activation via their TCR to become suppressive and to inhibit the proliferation of CD4+ or CD8+ T cells. Once activated, however, their regulatory/suppressor function was completely antigen-nonspecific, cytokine-independent yet cell contact dependent (Thornton, A. M., Shevach, E. M., J. Immunol. 164:183-190 (2000)). The exact mechanisms of suppression, notably the cell surface and/or short-range soluble molecules involved in the T-T interaction, have yet to be characterized. New in vitro data suggest that the CD4+CD25+ T cells inhibit the proliferation of responders by inhibiting their IL-2 production (Thornton, A. M., Shevach, E. M., J. Exp. Med. 188:287-296 (1998)). Recent in vivo studies suggest that the function of CD4+CD25+ T cells is crucially dependent on signaling via the CTLA-4/CD152 molecule which was found to be constitutively expressed on CD4+CD25+ T cells (Read, S. et al., J. Exp. Med. 192:295-302 (2000); Salomon, B. et al., Immunity 12:431-440 (2000); Takahashi, T. T. et al., J. Exp. Med. 192:303-310 (2000)).

Although it has been evident for years that in rodents the CD4+CD25+ T cell population constitutes a unique lineage of "professional" regulatory/suppressor T cells which are crucial for the prevention of spontaneous autoimmune disease (Sakaguchi, S. et al., J. Immunol. 155:1151-1164 (1995)), it is unknown to date, whether CD4+4T cells exhibiting similar functional properties are naturally occurring in man. The removal and/or functional impairment of these cells in vivo in mice e.g. by anti-CD25 and/or anti-CTLA-A4 mAb treatment of animals induces various spontaneous autoimmune diseases AND rejection of tumors. The mechanism is that removal/impairment of these cells removes their negative control of autoreactive T cells so that these T cells become active. If one gives back the CD4+ CD25+ T cells by adoptive transfer into these animals regulation is restored and autoimmunity/tumor rejection is stopped.

As set forth above, it is totally unknown to date whether CD4+ T cells exhibiting similar functional properties are naturally present in man. The preparation of human T cells with regulatory properties, which are, however, no CD4+ CD25+ T cells is known in the art. E. g. Jonuleit, H. et al., J. Exp. Med 192:1213-1222 (2000) describe the induction of regulatory T cells from human naïve T cells by repetitive stimulation with immature dendritic cells. Most of this work was done with T cells from cord blood which is the richest source of truly naïve T cells. It is to be noted that CD4+ CD25+ T cells are constitutively detectable in the human blood from early time points on. The subject of Jonuleit et al. is not a naturally occurring population. De Jong, P. et al., Int. Immunol. 6:631-638 (1994) describe the effect of TGF-β1 on naïve and memory CD4+ T cells. A differential effect is shown, with stimulatory effect on primarily activated CD45 RA+ CD4+ T cells. Proliferation of CD45 RO+ CD4+ T cells or secondary stimulated CD45 RO+ cells is suppressed. In the case of CD45 RA+ T cells TGF-β leads to an increased mean of fluorescens of CD25. The effects described here solely relate to proliferation of T cells. A regulatory capacity of naïve TGF-β treated T cells is not shown.

Surprisingly it was now found that CD4+CD25+, primarily CD45RO+ T cells (mean 6% of CD4+ T cells), hereinafter shortly referred to as "CD4+CD25+ T cells", are present in human blood, in particular the peripheral blood of adult healthy volunteers. In the past T cells exhibiting the phenotype (i.e., suppressive/regulatory CD4+CD25+ T cells) have been known for years but they were misinterpreted to be conventional memory cells (Kanegane, H. et al., Int. Immunol., 3:1349-1356 (1991); Taka, K. et al., Immunol. 72:15-19 (1990); Jackson, A. L. et al., Clin. Immunol. Innunopathol. 54:126-133 (1990)). In contrast to previous reports the human CD4+CD25+ T cells are not conventional memory cells but rather regulatory cells exhibiting functional properties identical to their rodent counterparts. CTLA-4 (CD152), for example, which is essential for the in vivo suppressive activity of CD4+CD25+ T cells, was constitutively expressed, and remained strongly upregulated after stimulation. The cells were non-proliferative to stimulation via their TCR, but the anergic state was partially reversed by IL-2 and IL-15. Upon stimulation with allogeneic (but not syngeneic) mature dendritic cells or plate-bound anti CD3+ anti-CD28 the CD4+CD25+ T cells released IL-10, and in coculture experiments suppressed the activation and proliferation of CD4+ and CD8+ T cells. Suppression proved IL-10 independent, yet contact dependent as in the mouse. The identification of regulatory CD4+CD25+ T cells has important implications for the study of tolerance in man, notably in the context of autoimmunity, transplantation, and cancer.

SUMMARY OF THE INVENTION

The present invention provides
(1) suppressive and/or regulative human CD4+CD25+ T cells;
(2) a method for expanding CD4+CD25+ T cells as defined in (1) above, which method comprises stimulating the cells with a T cell stimulating agent or with antigen-presenting cells ex vivo and in vivo;
(3) expanded human CD4+CD25+ T cells obtainable by the method as defined in (2) above, preferably by the ex vivo method defined in (2) above;
(4) a pharmaceutical composition comprising the human CD4+CD25+ T cells as defined in (1) or (3) above;
(5) use of CD4+CD25+ T cells as defined in (1) or (3) above for preparing a regulatory medicament;
(6) a method to identify, monitor and/or remove CD4+CD25+ T cells from human blood and other tissues ex vivo or in vivo, which method comprises
(i) utilizing agents/ligands specifically binding to the CD4, and/or CD25, and/or CTL-A4 (CD154) entities on the T cells, preferably anti-CD4 and/or anti-CD25, and/or anti-CTL-A4 antibodies, and/or
(ii) utilizing immunoadsorption methods; and/or
(iii) utilizing a stimulating agent or antigen presenting cells as defined in (2) above;
(7) use of a T cell stimulating agent or antigen presenting cells as defined in (2) above for preparing an agent to induce regulatory CD4+CD25+ T cells in vivo, preferably for preparing an agent for treating autoimmune diseases in a patient;
(8) use of CD4+CD25+ T cells as defined in (1) or (3) above
(a) in assays that will allow to identify other growth and/or functionally modifying (inhibitory/enhancing)/apoptotic or anti-apoptotic factors
(b) for identifying molecules expressed by the CD4+CD25+ T cells including identification of novel molecules on said cells, or if presenting molecules which are deemed pharmaceutically active, or
(c) for identifying precursor cells or progeny of the regulatory CD4+CD25+ T cells;
(9) use of the enriched CD4+CD25+ T cells of (1) above or the expanded T cells of (3) above for preparing an agent for adoptive transfer therapy, an agent for treating diseases with enhanced immunity including but not limited to autoimmune diseases, or an agent for preventing/treating transplantation reactions such as graft versus host disease and graft rejections;
(10) method for adoptive transfer therapy which comprises injecting/infusing back into the patients enriched/expanded autologous or non-autologous regulatory CD4+CD25+ T cells as defined in (1) or (3) above to prevent or treat any immune reactions that are too strong and/or pathogenic, or to prevent/treat transplantation reactions such as graft versus host disease and graft rejections;
(11) a method for preparing CD4+CD25+ T cells with a particular desired antigen-specific T cell receptor which comprises
(i) activating/stimulating/expanding the CD4+CD25+ T cells according to (1) above with antigen presenting cells, preferably immature or mature dendritic cells (DC), presenting said antigen in vitro or in vivo; or
(ii) utilizing a ligand/antibody to a particular T cell receptor expressed on (subsets of) CD4+CD25+ regulatory T cells, or a MHC-peptide complex binding to a particular T cell receptor on (subsets of) CD4+CD25+ T cells;
(12) CD4+CD25+ T cells obtainable by the method as defined in (11) above, or by transfection of a T cell receptor of desired antigen specificity into ex vivo isolated or expanded T cells;
(13) pharmaceutical composition comprising the T cells of (12) above, preferably said pharmaceutical composition being suitable to treat diseases with enhanced immunity including, but not limited to, autoimmune diseases, graft versus host disease and graft rejections; and
(14) use of agents specifically binding to the CD4 and/or CD25 and/or CTL-A4 (CD154) entities on the T cells, including but not limited to ligands/antibodies, such as anti-CD25 and/or anti-CTL-A4 mAb, or antibodies or MHC-peptide complexes or other ligands binding to T cell receptors on (subsets of) CD4+CD25+ T cells for preparing a medicament for removal or functional impairment of CD4+CD25+ T cells in vivo in order to enhance immune responses, including dampen regulation by CD4+CD25+ T cells in vivo, for example, to enhance tumor immunity.

DETAILED DESCRIPTION OF THE INVENTION

Figure 1A:
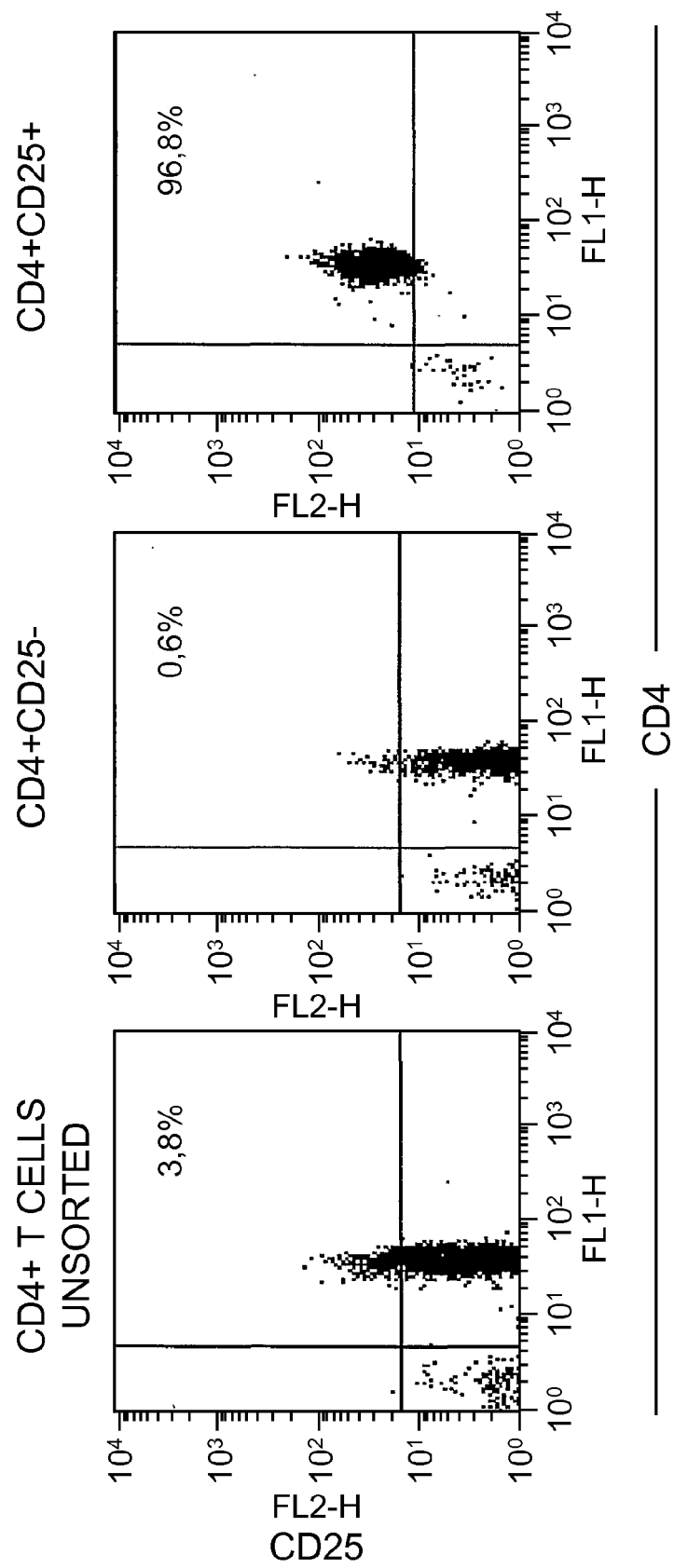
FIG. 1 shows that CD4+CD25+ T cells exhibit distinct phenotypical differences as compared to CD4+CD25− T cells.

The embodiments (1) to (14) of the invention are hereinafter described in more detail:

(A) The phenotypical characterization of the human CD4+CD25+ T cells now allows the identification, monitoring (e.g. by FACS), isolation and removal of these cells from human blood and other tissues ex vivo (hereinafter occasionally referred to as "in vitro") or in vivo. This isolation or removal can be achieved by contacting the human blood or other tissues with suitable agents ex vivo. Suitable agents are in particular anti-CD4, anti-CD25, anti-CTL-A4 (CD154) antibodies, etc.

(B) The CD4+CD25+ T cells can be expanded ex vivo by stimulation of the cells by treatment with suitable T cell stimulating agents or with antigen presenting cells (hereinafter shortly referred to as "APCs"). Suitable T cell stimulating agents suitable for the methods of (2) and (6) above include, but are not limited to, compositions comprising (a) anti-CD3 and/or anti-CD28 ligands/monoclonal antibodies (mAb) including superagonistic antibodies; (b) a ligand/antibody to T cell receptors on the surface of CD4+CD25+ T cells or to T cell receptor components; or (c) MHC-peptide complexes binding to the T cell receptors expressed on the surface of regulatory T cells; or (d) PMA (as well as other phorbolester)+ionomycin (or other calcium ionophores).

"Ligand" or "ligands" in accordance with the present invention relates to all kinds of compounds capable of binding to specific molecules (including polynucleotides and polypeptides such as cell receptors, CD25, CTL-A4, etc.). A preferred ligand is a monoclonal antibody or a fragment thereof. The terms "ligand" and "antibody" are used interchangeable throughout the application text.

Suitable APCs include autologous or non-autologous or artificial antigen-presenting cells (e.g. dendritic cells (for the preparation of dendritic cells see e.g. WO 93/20185, WO 97/29182 and EP-A-0 922 758), etc.). Said T cell stimulating agents and antigen-presenting cells can be used together with IL-2 or IL-15 or a combination thereof. Instead of IL-2/IL-15, other cytokines that use the gamma chain common to several cytokine receptors can also be used (including, but not restricted to, IL-7 and IL-9). Furthermore, IFN alpha and IL-10, which are known to promote the generation of other regulatory cells (Groux, H. et al., Nature 389:737-742 (1997); Roncarolo, M. G., J. Exp. Med. 193:F5-F9 (2001)) also promote the generation/expansion of these cells. Finally, other methods for polyclonal or oligoclonal (e.g. by superantigens) T cell stimulation are also applicable (anti-CD3 and/or anti-CD28 ligands/antigens including superagonistic antibodies; PMA+ionomycin; etc.). These stimulating agents or antigen presenting cells may be used for the expansion in amounts well-known for a person skilled in the art.

(C) The identification of the $CD4^+CD25^+$ T cells also allows to monitor and expand $CD4^+CD25^+$ T cells in vivo (e.g. by administering the T cells stimulating agents defined above, such as IL-2+IL-15 or IL-10+IFNα to patients, with or without the dendritic cells/antigen presenting cells) to induce regulatory T cells e.g. to fight autoimmune diseases.

(D) The $CD4^+CD25^+$ T cells or expanded $CD4^+CD25^+$ T cells of (1) or (3) above can be used in assays that will allow to identify other growth and/or functionally modifying (inhibitory/enhancing)/(apoptotic or anti-apoptotic) factors that can be used in vitro or in vivo (e.g. to stimulate or to remove or functionally disturb the $CD4^+CD25^+$ T cells). These T cells are also suitable for identifying molecules expressed by the $CD4^+CD25^+$ T cells by methods such as but not restricted to mAb generation, proteomics, DNA chip analysis, subtractive hybridization (in particular (a) identification of "novel", i.e., hitherto unknown, molecules, or (b) if these molecules are suitable pharmaceutical target structures, to therewith develop novel stimulating, inhibiting or apoptosis-inducing medicaments, for "switching on" or "switching off" of $CD4^+CD25^+$ T cells in vitro and in vivo) and for identifying precursor cells or progeny of the regulatory $CD4^+CD25^+$ T cells.

(E) The $CD4^+CD25^+$ T cells or expanded $CD4^+CD25^+$ T cells of (1) or (3) above can be used in adoptive transfer therapy, i.e. inject/infuse back into the patients enriched/expanded autologous or non-autologous regulatory T cells to prevent or treat any immune reactions that are too strong and/or pathogenic, i.e. to treat autoimmunity in its broadest sense (including but not limited to classical autoimmune diseases such as lupus erythematosus, rheumatoid arthritis, multiple sclerosis, pemphigus vulgaris or thyroiditis as well as diseases that have at least some autoimmune aspect in their pathogenesis such as vitiligo, atopic dermatitis, psoriasis vulgaris, etc.). Also to prevent/treat transplantation reactions such as GVHD (graft versus host disease) and graft rejections.

(F) The $CD4^+CD25^+$ T cells or expanded $CD4^+CD25^+$ T cells of (1) or (3) above (as well as the expansion method defined in (2) above, the pharmaceutical composition of (4) above and the use of (5) and (7) to (9) above can be used in conjunction with immature or mature dendritic cells (DC) (or other antigen presenting cells including artificial ones) that are or are not pulsed/loaded/fed with tissue or any other antigen (defined or undefined) in order to activate/stimulate/expand the $CD4^+CD25^+$ T cells in vitro or in vivo, to generate/expand $CD24^+CD25^+$ T cells with a particular desired antigen-specific TCR (T cell receptor). Examples of defined antigens are autoantigens (e.g. desmoglein 3 in the case of pemphigus vulgaris, melanA or tyrosinase in case of vitiligo; thyroglobulin in case of thyroiditis) or foreign antigens (e.g. pathogen-derived antigens such as Hepatitis C, etc.) or alloantigens/transplantation antigens. Examples of undefined antigens are tissue or cell-derived antigens (eg in the form of necrotic or apoptotic cells or tissue derived RNA or hybrids between cells of interest and dendritic cells/antigen presenting cells or other forms of delivery of undefined antigens into dendritic cells or other antigen presenting cells) or pathogen-derived antigens. Autologous or non-autologous $CD4^+CD25^+$ T cells and/or dendritic cells can be used.

(G) The agents specifically binding to the CD4 and/or CD25 and/or CTL-A4 (CD154) entities on the T cells as defined in (14) above can be used to remove and to monitor removal of $CD4^+CD25^+$ T cells in vivo e.g. by anti-CD25 and/or anti-CTL-A4 mAb (unmodified or modified e.g. conjugated to toxins) or by immunoadsorption (blood is flowing through columns and $CD4^+CD25^+$ T cells are removed by solid phase-bound antibodies directed to molecules expressed on the surface of $CD4^+CD25^+$ T cells e.g. anti-CD25) in order to enhance immune responses, e.g. dampen regulation by $CD4^+CD25^+$ T cells in vivo, for example, to enhance tumor immunity.

(H) In another preferred embodiment of the invention the expanded (i.e. activated) $CD4^+CD25^+$ T cells of (3) above (and also the T cells of (1) and (12) above) may be fixated. Such fixated T cells can be obtained by ex vivo treatment of the (expanded) T cells with a suitable fixation agent including, but not limited to, paraformaldehyde, etc. Preferably the fixation is performed by suspending the cells in a 0.5 to 5% (w/w) aqueous paraformaldehyde solution, most preferably in an about 2% (w/w) paraformaldehyde solution, for 15 min to 3 h, most preferably for 1 h, followed by appropriate washing steps.

(I) The $CD4^+CD25^+$ T cells utilized in the medicament of (5) above in the agents of (9) and (14) above, or the method of (10) above can be autologous or non-autologous regulatory T cells. In case of non-autologous regulatory T cells it is preferred that the T cells are fixated as mentioned in (H) above.

(J) The pharmaceutical composition of (4) and (13) above, the medicament of (5) above, the agents of (7), (9) and (14) above and the T cells utilized in the methods of (6), (8) and (10) above may contain further ingredients such as pharmaceutically/diagnostically suitable carriers, solvents, diluents and additives known to the person skilled in the art. The concentration of these ingredients are to be adapted for respective purpose by the person skilled in the art.

The concept of suppressor or immunoregulatory T cells has been revitalized during the past few years by the better delineation of several regulatory cell types in rodents, the mutual relationship of which is not yet finally defined. The so-called Tr1 and Th3 cells mediate bystander suppression—without need for direct cell contact—by the secretion of high levels of IL-10 and TGF-β, respectively (Groux, H. et al., Nature 389:737-742 (1997); Fukaura, H. et al., J. Clin. Invest. 98:70-77 (1996)). The best characterized and apparently most important regulatory T cell population identified so far are the CD4$^+$CD25$^+$ T cells. They occur naturally in rodents (representing about 10% of CD4$^+$ cells in lymphoid organs), are characterized by constitutive expression of CD25 (IL-2R-alpha), and are clearly of crucial importance for maintaining tolerance and preventing autoimmune disease in vivo. Surprisingly, a cell population exhibiting equivalent properties has not been described in humans to date. Here we have demonstrated, that the CD4$^+$CD25$^+$ T cells in human blood that previously had been considered to represent conventional memory T cells (Kanegane, H. et al., Int. Immunol. 3:1349-1356 (1991); Taka, K. et al., Immunol., 72:15-19 (1990); Jackson, A. L. et al., Clin. Immunol. Innunopathol. 54:126-133 (1990)) in fact appear to be the exact human counterpart of the unique CD4$^+$CD25$^+$ regulatory T cells that have been known and studied for many years in rodents. We were able to isolate the CD4$^+$CD25$^+$ T cells from adult blood in sizeable quantities (average 6% of CD4$^+$ T cells) so that a detailed study and comparison to CD4$^+$CD25$^-$ T cells could be undertaken. It turned out that the human cells share the key phenotypical and functional features with the murine CD4$^+$CD25$^+$ immunoregulatory T cells. The most interesting and previously unidentified phenotypical feature was that the CTLA-4 molecule (CD152) was already constitutively expressed (at high levels intracellularly, and at low levels at the surface) by the human CD4$^+$CD25$^+$ T cells, was further upregulated after stimulation via the TCR and maintained at high surface levels for at least a week thereafter (in sharp contrast to CD4$^+$CD25$-$ T cells that expressed CTLA-4 de novo upon stimulation, and only very transiently as described (Thompson, C. B., Allison, J. P., Immunity, 7:445-450 (1998); Chambers, C. A. et al., Immunol. Rev. 153:27-46 (1996)). The expression pattern of CTLA-4 by CD4$^+$CD25$^-$ already supported their relationship to the murine CD4$^+$CD25$^+$ regulatory T cells as these cells constitutively express CTLA-4 as a molecule essential for their in vivo suppressive activity (Read, S. et al., J. Exp. Med. 192:295-302 (2000); Salomon, B. et al., Immunity, 12:431-440 (2000)). Like their murine counterparts the human CD4$^+$CD25$^+$ T cells showed almost no proliferation upon stimulation, neither in response to polyclonal activation by plate-bound anti CD3+anti CD28 nor following (even repetitive) stimulation with the most potent natural immunostimulatory cells, i.e. mature (allogeneic) DC. When these stimuli were combined with high doses of IL-2 (500 U/ml) anergy was partially reversed as described in the mouse (Thornton, A. M., Shevach, E. M., J. Immunol., 164:183-190 (2000)). A novel finding was that IL-15 at high doses (50-100 ng/ml) induced comparable proliferation, and that the combined action of IL-2 and IL-15 even at lower doses (10 U/ml and 10 ng/ml, respectively) had a strong synergistic action and induced vigorous proliferation. This might proof important, as expansion of CD4$^+$CD25$^+$ T cells is vital for potential therapeutic applications and cloning of these cells for further more detailed studies (including mechanistic and molecular ones). Of interest was that neutralizing anti IL-10 mAb failed to promote proliferation indicating that the release of IL-10 by these cells was not causing anergy in an autocrine fashion. In coculture experiments the CD4$^+$CD25$^+$ T cells displayed another key feature in that they suppressed yet only upon activation via their own TCR the proliferation of CD25$^-$CD4$^+$ or CD8$^+$ T cells in a contact- and dose-dependent, yet cytokine-independent manner. Our ex vivo system has not allowed us to investigate whether the suppression is completely antigen-nonspecific as has recently been shown in the mouse by taking advantage of TCR transgenic mice (Thornton, A. M., Shevach, E. M., J. Immunol., 164:183-190 (2000)). Respective mechanistic studies might be possible, however, by employing our IL-2+IL-15 approach for the expansion of these cells.

It is most remarkable that a recent report has shown that T cells with regulatory properties and a phenotype virtually identical to the CD4$^+$CD25$^+$ T cells we have isolated ex vivo from human blood can be generated in vitro by repetitive stimulation of human naive T cells with immature DC (Jonuleit, H. et al., J. Exp. Med., 192:1213-1222 (2000)). In the mouse CD4$^+$CD25$^+$ regulatory T cell populations are continuously generated in the thymus (Itoh, M. et al., J. Immunol. 162:5317-5326 (1999)), yet the maintenance of regulatory T cells in the periphery requires the presence of tissue-specific antigens and IL-2 (25, 26). Based on the two supplementary findings (Jonuleit, H. et al., J. Exp. Med., 192:1213-1222 (2000)) it is certainly tempting to speculate, that immature DC that have sampled peripheral tissues via the uptake of apoptotic antibodies (Steinman, R. M. et al., J. Exp. Med., 191:411-416 (2000); Roncarolo, M. G. et al., J. Exp. Med. 193:F5-F9 (2001)), and present universal or tissue-specific autoantigens, are responsible for the survival and possibly slight proliferation of thymic regulatory T cell emigrants. It is believed that the survival of the ex vivo isolated CD4$^+$CD25$^+$ regulatory T cells can be promoted by interaction with immature DC, and that the recently reported "generation" of CD4$^+$CD25$^+$ T cells from naïve T cells by immature DC in vitro (Jonuleit, H. et al., J. Exp. Med., 192:1213-1222 (2000)) possibly rather represents maintenance of survival of preexisting CD4$^+$CD25$^+$ in the initial inoculum. It is also of note that it was found that interaction of ex vivo isolated human CD4$^+$CD25$^+$ T cells with syngeneic mature DC was insufficient to activate their suppressive properties while allogeneic mature DC were potent inducers of regulation. This observation again suggests testable hypotheses. For example, will immature in contrast to mature syngeneic DC activate CD4$^+$CD25$^+$ T cells (suggesting that they carry some specific ligand for interaction), or will they do so only after ingestion of apoptotic bodies (suggesting that presentation of autoantigens is required)? Furthermore, can mature DC that present nominal recall antigens (e.g. influenza proteins/peptides) stimulate T cells both in the CD4$^+$CD25$^-$ T cell population and the CD4$^+$CD25$^+$ T suggesting that besides autoantigens also the recognition of foreign antigens could trigger regulation at inflammatory sites.

In summary, it was shown that a sizeable population (~6%) of CD4$^+$CD25$^-$ T cells exists in the peripheral blood of normal human adults that in contrast to previous belief do not represent conventional memory but rather regulatory T cells equivalent to the unique population of CD4$^+$CD25$^-$ "professional" suppressor/regulatory T cells that have been studied for years in rodents. The identification and characterization of the human CD4$^+$CD25$^+$ regulatory T cells will now allow for their monitoring in various disease states, and has important implications for understanding and treating autoimmunity, graft rejection, and cancer.

The invention is further explained by the following figures and examples which, however, are not intended to limit the invention:

FIGURES

FIG. 1: CD4$^+$CD25$^+$ T Cells exhibits distinct phenotypical differences to CD4$^+$CD25$^-$ T Cells. CD4$^+$ T cells were isolated from PBMC by negative MACS sorting, yielding highly purified untouched CD4$^+$ T cells. These cells were labeled with anti CD25 magnetic beads and sorted.

(A): Sorting resulted in virtually pure CD25$^+$ T cells. A representative result out of 20 independent standardized experiments is shown.

(B): The phenotype of CD4$^+$CD25$^+$, CD4$^+$CD25$^-$ and activated CD4$^+$CD25$^-$ T cells was analyzed as described in Materials & Methods. In addition, CD4$^+$CD25$^-$ T cells were activated with immobilized anti CD3+soluble anti CD28. After activation cells were labeled with anti CD25 magnetic beads and sorted. Results were similar in 5 independent experiments.

(C): CD4$^+$CD25$^+$ and CD4$^+$CD25$^-$ T cells were stained with anti CTLA-4 antibody at 37° C. for 2-h. Staining was performed ex vivo and at different time points after activation with immobilized anti CD3+soluble anti CD28. One representative result of 4 independent experiments is shown.

Figure 2A:
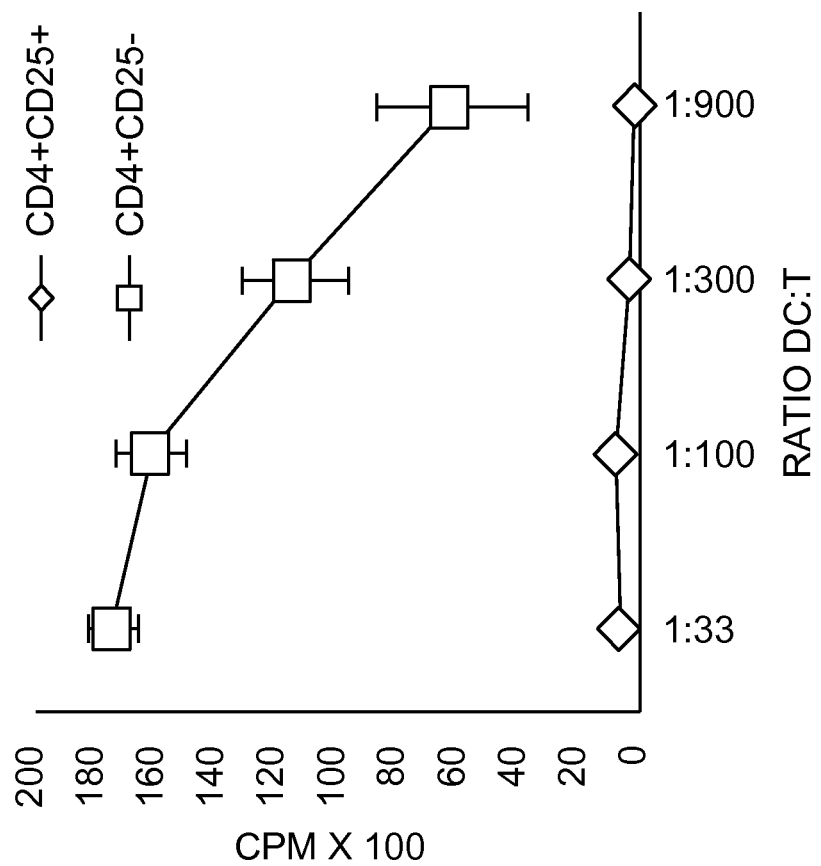
FIG. 2 shows that CD4+CD25+ T cells are nonproliferative/anergic to both allogeneic and polyclonal stimulation, which is partially reversed by the addition of IL-2 and/or IL-15, but not by neutralizing anti IL-10 antibodies.

FIG. 2: CD4$^+$CD25$^+$ T cells are nonproliferative/anergic to both allogeneic and polyclonal stimulation, which is partially reversed by the addition of IL-2 and/or IL-15, but not by neutralizing anti IL-10 antibodies.

(A): CD4$^+$CD25$^+$ and CD4$^+$CD25$^-$ T cells were isolated from adult blood by MACS sorting as in FIG. 1. 1×10$^5$ T cells/96 well were stimulated with different numbers of mature allogeneic DC. Proliferation of T cells (triplicate cultures) was determined by [$^3$H]Tdr incorporation. Results were similar in 6 independent experiments.

(B): Whole CD4$^+$, CD4$^+$CD25$^+$ and CD4$^+$CD25$^-$ T cells were treated as described in (A). Proliferation in triplicate cultures was determined by [$^3$H]Tdr incorporation (representative result of 5 independent experiments).

(C): MACS sorted CD4$^+$CD25$^+$ and CD4$^+$CD25$^-$ T cells were primed and restimulated every week with mature allogeneic DC from the same donor (DC:T cell ratio of 1:20). Proliferation (1×10$^5$ T cells/96 well) was determined by [$^3$H]Tdr incorporation. Similar results were obtained in 3 independent experiments.

(D): CD4$^+$CD25$^+$ and CD4$^+$CD25$^-$ T cells were stimulated with immobilized anti CD3 (10 µg/ml) and soluble anti CD28 (10 µg/ml) [upper panels] or with mature allogeneic DC [lower panels] as described in (A). 500 U/ml IL-2, 100 ng/ml IL-15, a mixture of 10 U/ml IL-2+1 ng/ml IL-15 or 10 µg/ml anti IL-10 were added at the onset of culture. [$^3$H]Tdr incorporation was measured after 5 days of culture. One of 3 independent experiments is shown. The addition of IL-2 and/or IL-15 in the absence of a polyclonal or allogeneic T cell stimulus did not induce significant proliferation in the CD25$^+$ or CD25$^-$ T cell subset (data not shown).

FIG. 3: CD4$^+$CD25$^+$ T Cells if stimulated via the TCR suppress the activation of CD4$^+$ and CD8$^+$ T Cells in a cell contact- and dose-dependent manner.

(A, B): MACS sorted total CD4$^+$ (A) and CD8$^+$ (B) T cells (10$^5$ T cells/96 well) were added to CD4$^+$CD25$^+$ T cells at the ratios indicated, and stimulated with allogeneic DC at a DC/CD4$^+$ or CD8$^+$ T cells ratio of 1:20. Proliferation was determined by [$^3$H]Tdr incorporation after 5 days. One of 5 independent experiments is shown.

(C): DC and CD4$^+$CD25$^+$ T cells were generated/isolated from the same donor (donor I). In addition, whole CD4$^+$ T cells and CD4$^+$CD25$^+$ T cells were isolated from another donor (donor II). 10$^5$ whole CD4$^+$ T cells/96 well were cultured with 5×10$^3$ DC/well (i.e. DC:T ratio=1:20; results were comparable at a DC:T ratio of 1:100, not shown). CD4$^+$CD25$^+$ T cells from donor I and donor II were then added, respectively. Proliferation was determined by [$^3$H] Tdr incorporation after 5 days of culture. Results representative of 3 independent experiments are shown as mean cpm of triplicate cultures.

(D): Whole CD4$^+$ T cells or CD4$^+$CD25$^+$ T cells were (10$^5$ T cells/96 well) stimulated with 5×10$^3$ allogeneic mature DC (DC:T ratio=1:20) (upper 2 panels). In addition, whole CD4$^+$ T cells were cocultured with CD4$^+$CD25$^+$ T cells at a ratio of 1:1 (10$^5$ T cells/96 well each) and stimulated with allogeneic DC again at a DC:T ratio of 1:20 in the presence or absence of 10 µg/ml anti IL-10, 2 µg/ml TGF-beta, 500 U/ml IL-2, 50 ng/ml IL-15 or a mixture of 10 µU/ml IL-2, 1 ng/ml IL-15. In a parallel Transwell approach the CD4$^+$CD25$^+$ T cells were stimulated with allogeneic DC (DC/T cell ratio of 1:20) in a Transwell chamber, and whole CD4+ T cell responders were put into the well together with allogeneic DC again at a DC:T ratio of 1:20. Proliferation after 5 days of culture was determined by [$^3$H]Tdr incorporation. One of four representative experiments is shown.

Figure 4A:
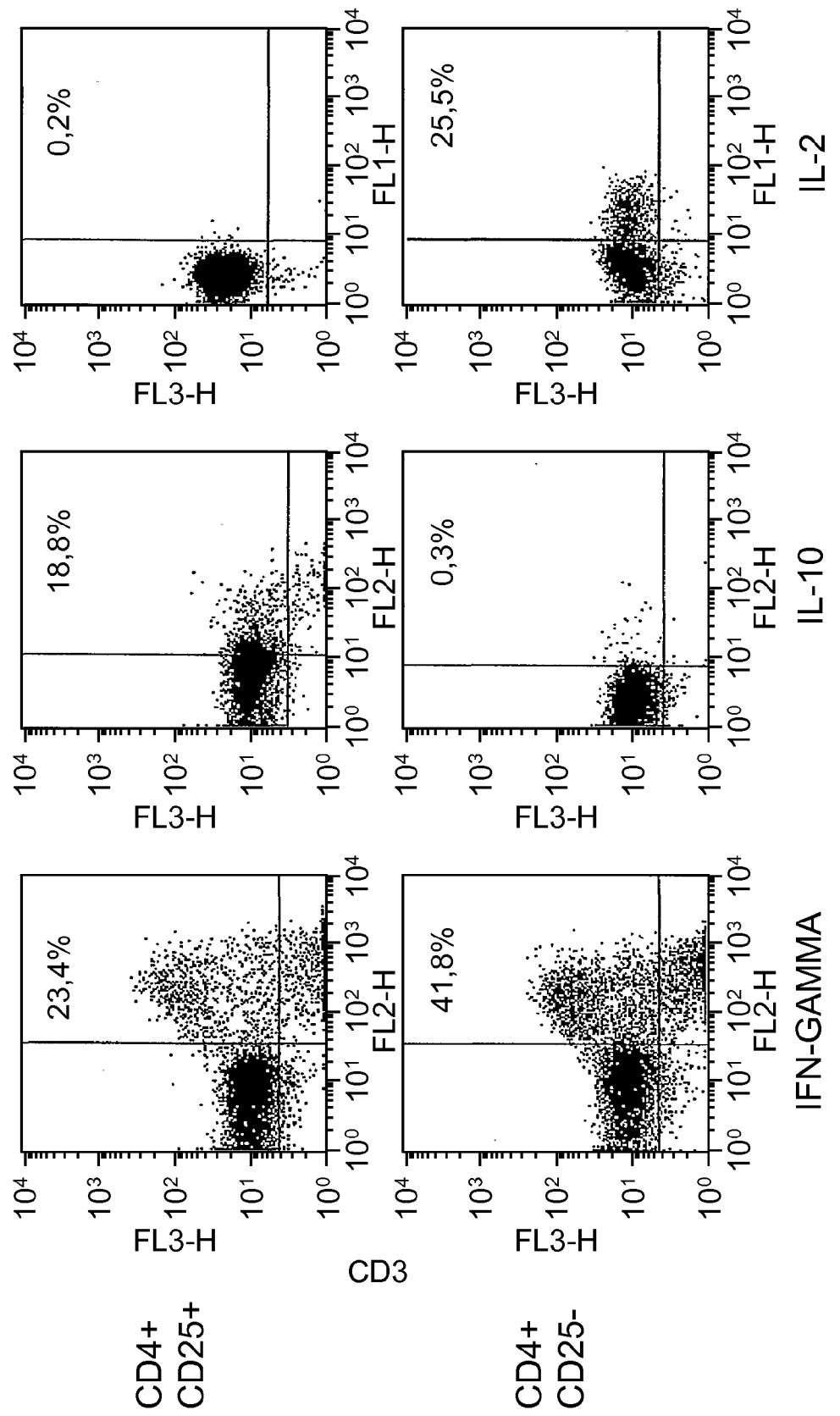
FIG. 4 shows that the cytokine profiles of CD4+CD25+ and CD4+CD25− T cells are different.
Figure 4B:
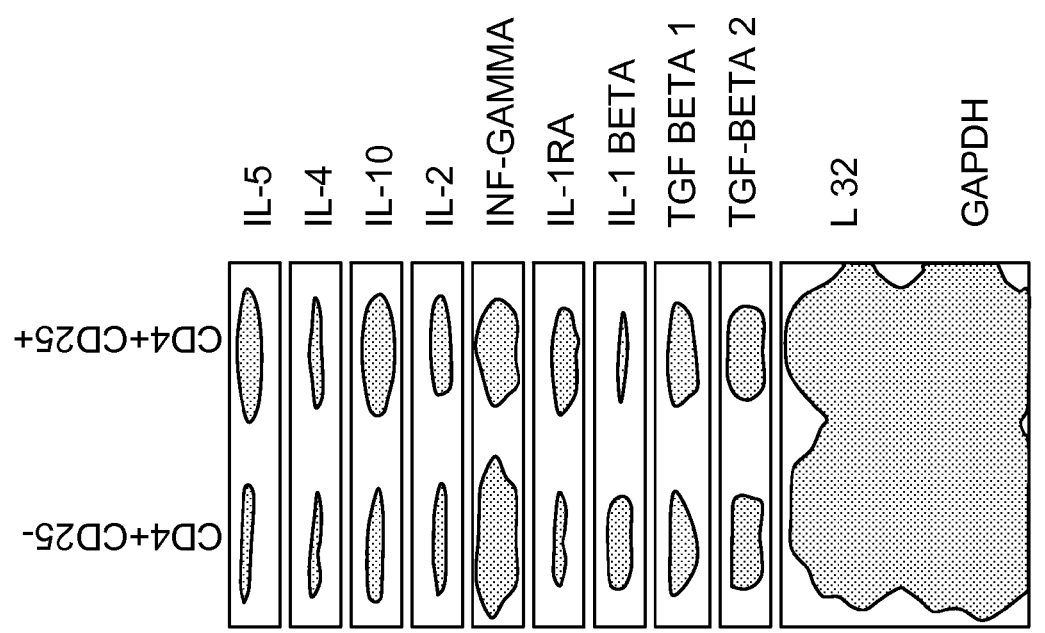

FIG. 4: Different cytokine profiles of CD4$^+$CD25$^+$ and CD4$^+$CD25$^-$ T cells.

(A): MACS sorted CD4$^+$CD25$^+$ and CD4$^+$CD25$^-$ T cells were stimulated with PMA (20 ng/ml) and A23187 Ca$^{2+}$ ionophore (500 µg/ml) for 6 h. Monensin (2 µM) was added for the last 5 h. Staining of CD3 surface expression was performed. Cells were washed, fixed, permeabilised and stained for detection of intracellular cytokines using FITC- or PE-conjugated specific antibodies. One of 5 independent experiments with similar results is shown. Results were identical when T cells were stimulated with platebound anti-CD3+soluble anti-CD28 AB (not shown).

(B): CD4$^+$CD25$^+$ and CD4$^+$CD25$^-$ T cells were activated with platebound anti CD3+soluble anti CD28. After 48 h of culture analysis of RNA expression was performed by RNase Protection assay.

(C): Cytokines in the supernatant were measured by ELISA (one of 5 independent experiments is shown).

Material and Methods

Culture Medium:

RPMI 1640 (Bio Whittaker) supplemented with 1% heat-inactivated autologous plasma, 20 µg/ml gentamicin (Merck) and 2 mM glutamine (Bio Whittaker) was used for the generation of dendritic cells (DC), X-VIVO-20 (Bio Whittaker) supplemented with 1% heat-inactivated single donor human serum, 20 µg/ml gentamicin (Merck) and 2 mM glutamine (Bio Whittaker) for T cell culture.

Cytokines:

All cytokines used in this study were recombinant human proteins. Final concentrations were: GM-CSF 1,000 U/ml (Leukomax™; Novartis), IL-4 800 U/ml (Sandoz), IL-2 (Proleukin; Chiron Corp.) and IL-15 (PeproTech) were used at the concentrations indicated; for DC maturation we used a cocktail consisting of IL-1β 2 ng/ml (Sigma); IL-6 1000 U/ml (Sandoz); TNF-α 10 ng/ml (Bender, Vienna), and PGE$_2$ 1 µg/ml (Sigma).

Antibodies:

For immunostaining PE- and FITC-conjugated Antibodies (Ab) (all from BD Pharmingen) against CD3, CD4, CD5, CD8, CD14, CD19, CD25, CD28, CD45 RA, CD45 RO, CD56, CD62L, CD80, CD83, CD86, CD95, CD95L, CD122, CD152, CD154, HLA-DR, and respective mouse and rat isotype controls were employed. Ab used for intracellular cytokine staining to were FITC- and PE-conjugated anti IL-2 (MQ1-17H12), anti IL-4 (8D4-8), anti IL-10 (JES3-19F1) and anti IFN-γ (4S.B3), all from BD Pharmingen. Unconjugated anti IL-10 (JES3-19F1) (Pharmingen) and anti TGF-β (R&D Systems) were used for neutralization experiments, anti CD3 (UCHT1) and anti CD28 (CD28.2) for polyclonal activation of T cells.

Cytokine Assays:

T cells were stimulated with allogeneic DC or with platebound anti CD3 (10 µg/ml)+soluble anti CD28 (10 µg/ml) in X-VIVO-20+1% serum. Cytokine analysis was performed at different time points by analysis of supernatants with commercially available ELISA kits for human IL-2, IL-4, IL-10, IFN-γ and TGF-β (BD Pharmingen). For analysis of intracellular cytokine production T cells were either stimulated with PMA 20 ng/ml and $Ca^{2+}$ ionophore A23187 500 µg/ml (both from SIGMA) for 6 hours or with platebound anti-CD3 and soluble anti-CD28 Ab for 6 hours. Monensin, 2 µM (SIGMA) was added for the last 4 hours of culture. Cells were collected, washed, fixed and saponine permeabilized (Fix/perm solution, BD Pharmingen) and stained with cytokine specific Ab or isotype.

For cytokine mRNA analysis T cells were stimulated with platebound anti CD3 and soluble anti CD28 Ab. Cells were analyzed by RNase Protection assay template sets (BD Pharmingen).

Cell Isolation and DC Generation:

DC were generated from buffy coats or leukapheresis products (both obtained from the Department of Transfusion medicine from healthy donors after informed consent was given) as described (18,19). In brief, PBMCs were isolated by Ficoll density gradient centrifugation. Monocytes were isolated by plastic adherence and cultured in RPMI Medium, supplemented with IL-4 and GM-CSF. At day 6 a maturation cocktail (IL-1β, IL-6, $PGE_2$ and TNFα) was added. At day 7 nonadherent cells were harvested and constituted mature DC that were >90% double positive for costimulatory molecules (CD80, CD86) and CD83.

$CD4^+$ T cells were isolated from PBMC with a negative $CD4^+$ T cell isolation kit (Miltenyi Biotech). $CD4^+CD25^+$ T cells were isolated from the pure, untouched $CD4^+$ T cells using CD25 Microbeads (Miltenyi Biotech). Isolation of $CD8^+$ T cells was performed using a negative $CD8^+$ T cell isolation kit (Miltenyi Biotech). Purity was assessed by FACS.

Flow Cytometric Analysis: For immunofluorescence staining cells were washed, stained for 20 min at 4° C. with optimal dilution of each Ab. Cells were washed again and analyzed by flow cytometry (FACS Scan™ and CELL-Quest™ software; Becton Dickinson). For analysis of cell surface CD152 expression, cells were stained with the appropriate antibody for 2 hours at 37° C.

Proliferation Assays:

To assess proliferation of different $CD4^+$ subtypes $10^5$ sorted T cells were incubated in X-VIVO-20 with different numbers of DC or different concentrations of platebound anti CD3+soluble anti CD28 in 96-well plates. For assessment of regulatory properties $10^5$ bulk $CD4^+$ T cells were cultured with $5\times10^3$ (in some experiments also with $1\times10^3$) DC in 96-well plates. Purified $CD4^+CD25^+$ or $CD4^+CD25^-$ T cells were added at different concentrations. After 4-5 days of culture [3H]Tdr (37 KBq/well) was added for additional 16 h. Proliferation was measured using a liquid scintillation counter.

Transwell Experiments:

Transwell experiments were performed in 24-well plates. $10^6$ bulk $CD4^+$ T cells were stimulated with $5\times10^3$ DC. In addition, $10^6$ $CD4^+CD25^+$ or $CD4^+CD25^-$ T cells were either added directly to the culture or were placed in Transwell chambers (Millicell, 0.4 µm; Millipore). After 5 days of coculture T cells were transferred to 96-well plates ($10^5$ cells/well) in triplicates. Proliferation was measured after 16 h pulse with [3H]Tdr using a liquid scintillation counter.

EXAMPLES

Example 1: $CD4^+CD25^+$ T Cells Show a Reduced Proliferative Response to Both Allogeneic and Polyclonal Stimulation A low proliferative potential is highly characteristic of the well characterized regulatory $CD25^+CD4^+$ T cells in the murine system (Sakaguchi S. et al., J. Immunol., 155:1151-1164 (1995)). To analyze the proliferative capacity of human $CD4^+$ subpopulations $CD4^+$ T cells were magnetically sorted for their expression of CD25. By using a MACS CD4 negative selection kit and afterwards a positive selection for CD25 a more then 95% pure population of $CD4^+CD25^+$ T cells was obtained (FIG. 1A). These cells comprised around 6% (2.8-17.2%, n=20) of peripheral $CD4^+$ T cells in the blood of the healthy adults we studied.

Figure 2B:
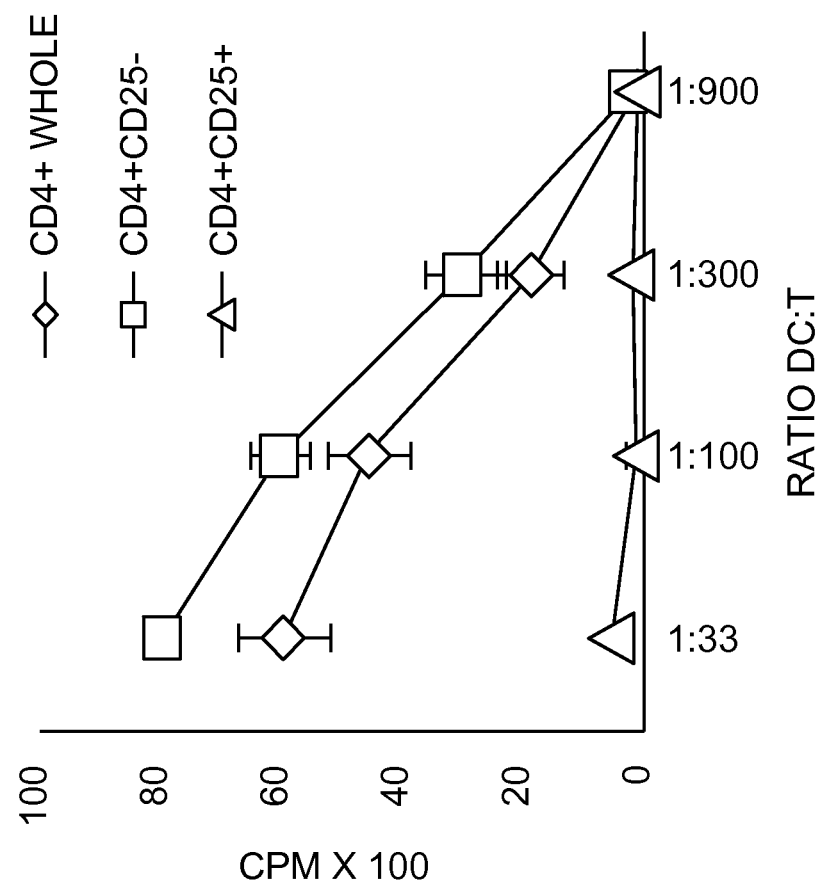

Mature DC are known as the most powerful antigen presenting cells (Bancherau, J., Steinman, R. M., Nature, 392:245-252 (1998)). Nevertheless, the $CD4^+CD25^+$ T cells exhibited virtually no proliferative response when stimulated in vitro with fully mature allogeneic DC in sharp contrast to the $CD4^+CD25^-$ T cells (FIG. 2A, B) or the whole $CD4^+$ population (FIG. 2B). Interestingly, the $CD4^+$ population depleted of $CD25^+$ T cells showed a higher proliferation when stimulated with allogeneic DC compared to the whole $CD4^+$ population (FIG. 2B).

Figure 2C:
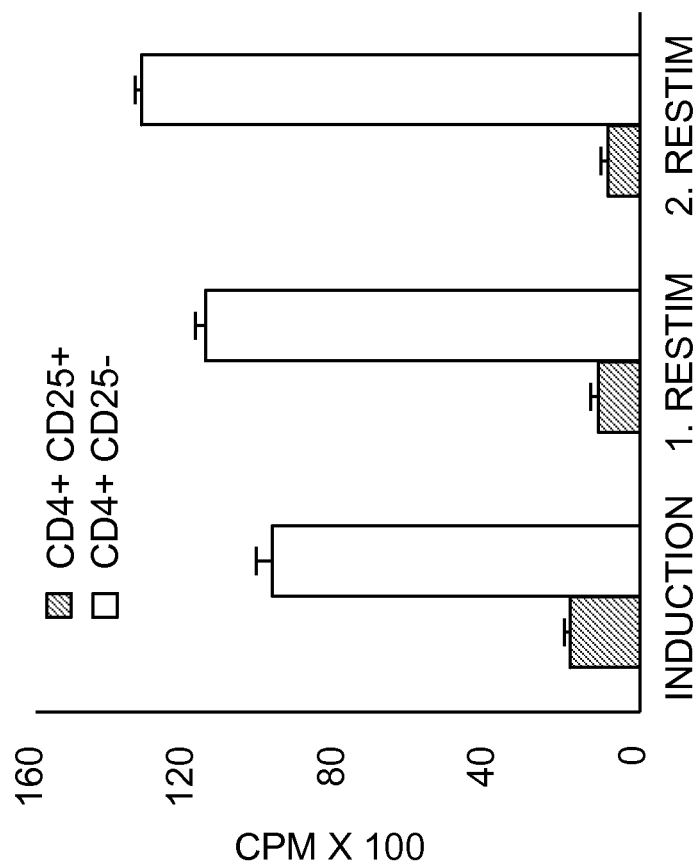

It was next determined whether the $CD4^+CD25^+$ T cells would possibly only proliferate upon repetitive stimulation by mature DC. After restimulation the proliferative response of $CD25^-$ T cells increased somewhat, whereas the response of $CD25^+$ T cells remained very low (FIG. 2C). Priming and restimulation by allogeneic mature DC resulted in a 30- to 50-fold expansion of the $CD25^-$ population after two rounds of restimulation. In contrast, there was no significant increase of the $CD25^+$ population (data not shown). A slightly (~10%) decreased absolute number of $CD4^+CD25^+$ T cells was harvested as compared to the initial inoculum after the repetitive stimulation in the apparent absence of significant apoptosis or necrosis (data not shown).

The exceedingly low proliferative response of $CD4^+CD25^+$ T cells was also apparent when these cell populations were polyclonally stimulated with platebound anti CD3+soluble anti CD28 (FIG. 2D). To test whether the T cell growth factors IL-2 and IL-15 could affect the proliferative potential various doses were added to $CD4^+CD25^+$ and $CD4^+CD25^-$ T cells that were stimulated either with immobilized anti CD3+soluble anti CD28 (FIG. 2D, upper panels) or with mature allogeneic DC (FIG. 2D, lower panels). A series of pilot experiments revealed that IL-2 enhanced the proliferation of $CD25^+$ T cells only at high doses (100-1000 U/ml). IL-15 had a similar effect, again only at very high doses of 50-100 ng/ml. When both cytokines were mixed, they had strong synergistic effects and doses of 10 U/ml IL-2 plus 10 ng/ml IL-15 were sufficient to promote the proliferation of $CD4^+CD25^+$ T cells. The addition of IL-2 and/or IL-15 in the absence of a polyclonal or allogeneic T cell stimulus did not induce significant proliferation in the $CD25^+$ or $CD25^-$ T cell subset (data not shown).

Figure 1B:
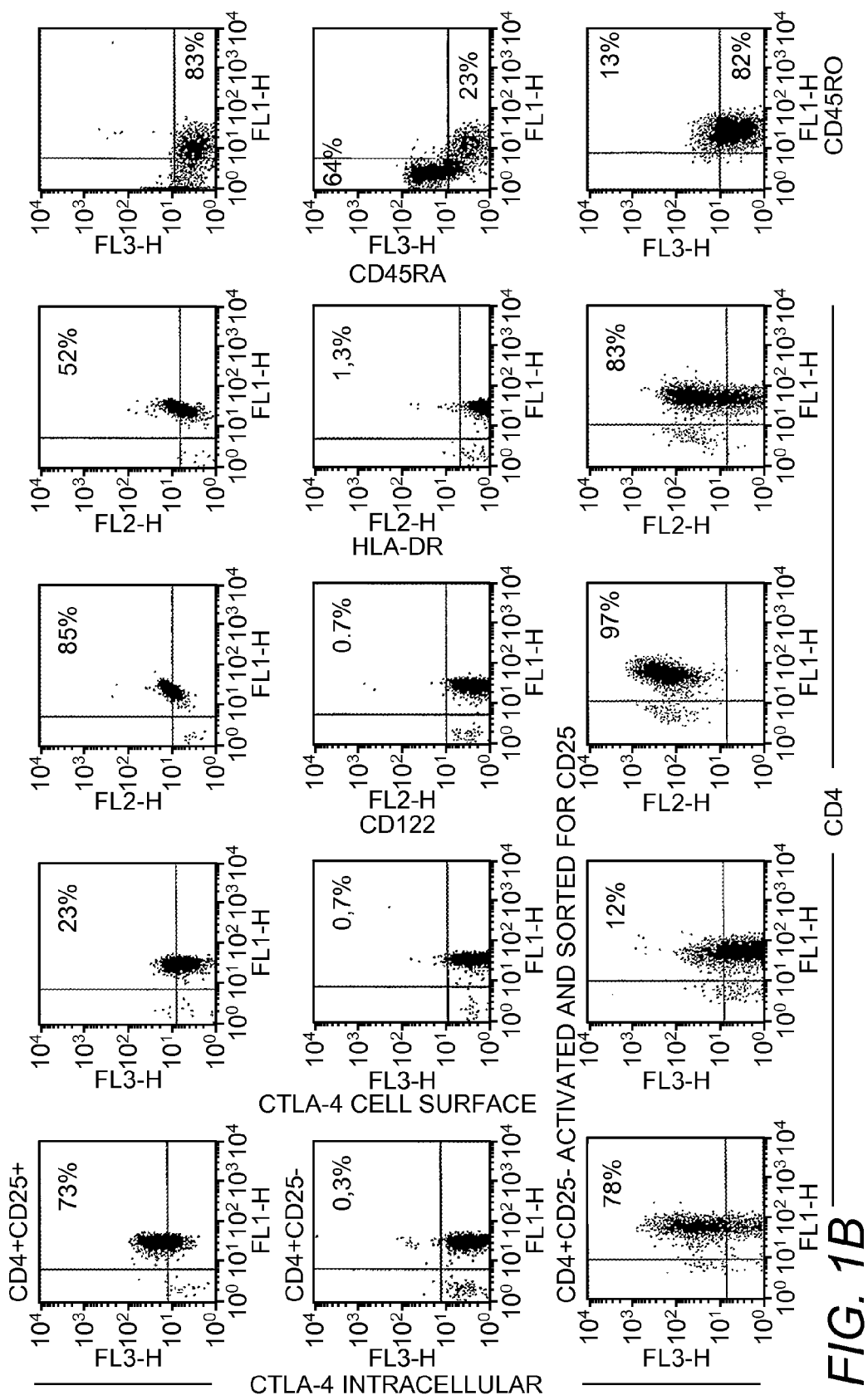
Figure 1C:
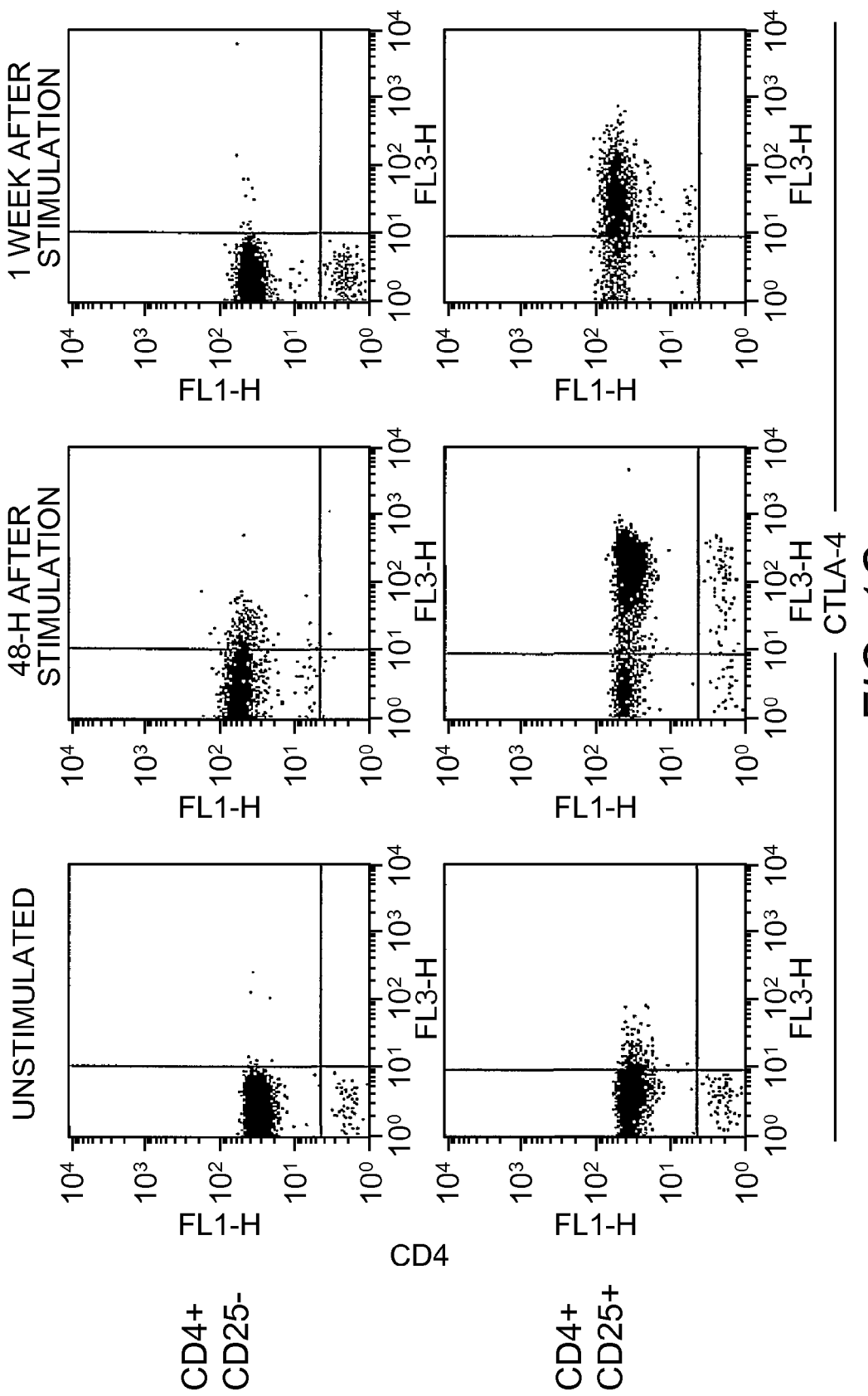

Example 2: $CD4^+CD25^+$ T Cells Exhibit Distinct Phenotypical Differences to $CD4^+CD25^-$ T Cells To further characterize the $CD25^+CD4^+$ T cell population, the expression of various surface molecules on $CD4^+CD25^+$, CD4+CD25− was compared with that on stimulated CD4+ CD25− T cells (FIG. 1B). All three populations showed homogenous expression of CD3 and CD4. No contaminating cells such as monocytes, B cells, CD8+ T cells or NK cells could be observed by FACS analysis (data not shown). Without prior stimulation, i.e. ex vivo the CD25+ population already expressed high levels of intracellular, and low levels of cell surface CTLA-4 (CD152). Ex vivo isolated CD4+ CD25+ T cells furthermore constitutively expressed CD122 (IL-2R beta chain), HLA-DR (~50%) and consisted primarily (~80%) of CD45RO cells resembling a memory T cell phenotype. In sharp contrast, the ex vivo isolated CD4+ CD25− T cells did not express CTLA-4 (neither intracellularly nor on the surface), CD122, or HLA-DR, and more cells expressed CD45RA rather than CD45RO. Following activation with plate bound anti-CD3+soluble anti-CD28, however, most CD4+CD25− became strongly CD25+ (the level of CD25 expression was about 1 log higher, compared to the CD4+CD25+ T cells, data not shown), and displayed high levels of HLA DR and CD122 (again about 1 log higher compared to CD4+CD25+ T cells) as to be expected. In addition, both intracellular and surface CTLA-4 was upregulated within 24-48 h yet quickly downregulated thereafter (FIG. 1C) as expected. The kinetics of CTLA-4/CD152 expression proved strikingly different when CD4+CD25+ T cells were stimulated. These cells also upregulated their (constitutively already present albeit low) CD152 surface expression, yet the strong expression of CD152 remained constant for a period of more than 1 week (FIG. 1C). Staining with several other mAb such as anti CD28, CD62L, CD69, CD95, CD95L, CD154 (CD40L) did not reveal reproducible and significant differences between CD4+CD25+ and CD4+CD25− T cells.

Examples 3: CD4+CD25+ T Cells if Stimulated Via the TCR Suppress the Activation of CD4+ and CD8+ T Cells in a Cell Contact- and Dose-Dependent Manner To analyze the putative regulatory properties of CD25+ T cells coculture experiments were performed. In a first series of tests we isolated from a particular donor both the total CD4+ population and the CD25+ and CD25− fractions. Whole CD4+ T cells were then mixed with CD4+CD25+ or CD4+CD25− T cell subpopulations at indicated ratios, and stimulated with allogeneic mature DC (FIG. 3A). CD4+ CD25+ T cells significantly inhibited the proliferation of whole CD4+ T cells, and at a 1:1 ratio virtually blocked it (cpm then represented the background levels of CD25+ T cell proliferation, see FIG. 2A-D). The addition of CD25− T cells instead of CD25+ T cells slightly enhanced proliferation (not shown). As CD4+CD25− rapidly expressed CD25 and CD122, i.e. both chains of the IL-2R, upon polyclonal (see FIG. 1B) as well stimulation by allogeneic DC (data not shown) this finding indicated that the suppressive activity of the CD4+CD25+ T cell subset was not simply due to consumption or passive adsorption of IL-2 via their IL-2R. CD4+CD25+ T cells exerted also a suppressive activity on whole CD8+ T cells albeit downregulation was less intense (FIG. 3B).

In a further set of experiments it was determined whether activation of CD4+CD25+ T cells by syngeneic DC was sufficient for induction of their regulatory properties. To this end mature DC and CD4+CD25+ T cells were generated/isolated from the same donor (donor I). In addition, whole CD4+ T cells as well as the CD4+CD25+ T cell subset were isolated from another donor (donor II). The whole CD4+ T cells (donor II) were then stimulated with allogeneic mature DC (donor I) in the absence (FIG. 3C, CD4+ only) or presence of various numbers of CD4+CD25+ T cells isolated from either donor I or donor II (FIG. 3C). Whole CD4+ T cells from donor II proliferated vigorously as expected when stimulated with allogeneic, donor I-derived DC (FIG. 3C, CD4+ only). In the presence of donor I-derived CD4+CD25+ T cells (i.e. syngeneic to the DC used) the proliferation (i.e. alloreactivity) of whole donor II-derived CD4+ T cells was not suppressed at all (FIG. 3C). Potent suppression occurred, however, when donor II-derived CD4+CD25+ T cells (i.e. allogeneic to the DC used) were added (FIG. 3C). Suppression was also observed in experiments where DC, whole CD4+ T cells, and CD4+CD25+ T cells were derived from three different donors. These data indicated that TCR-mediated activation of CD4+CD25+ T cells was required to let them exert their regulatory function, and that syngeneic DC were insufficient to induce their suppressive activity.

Figure 3D:
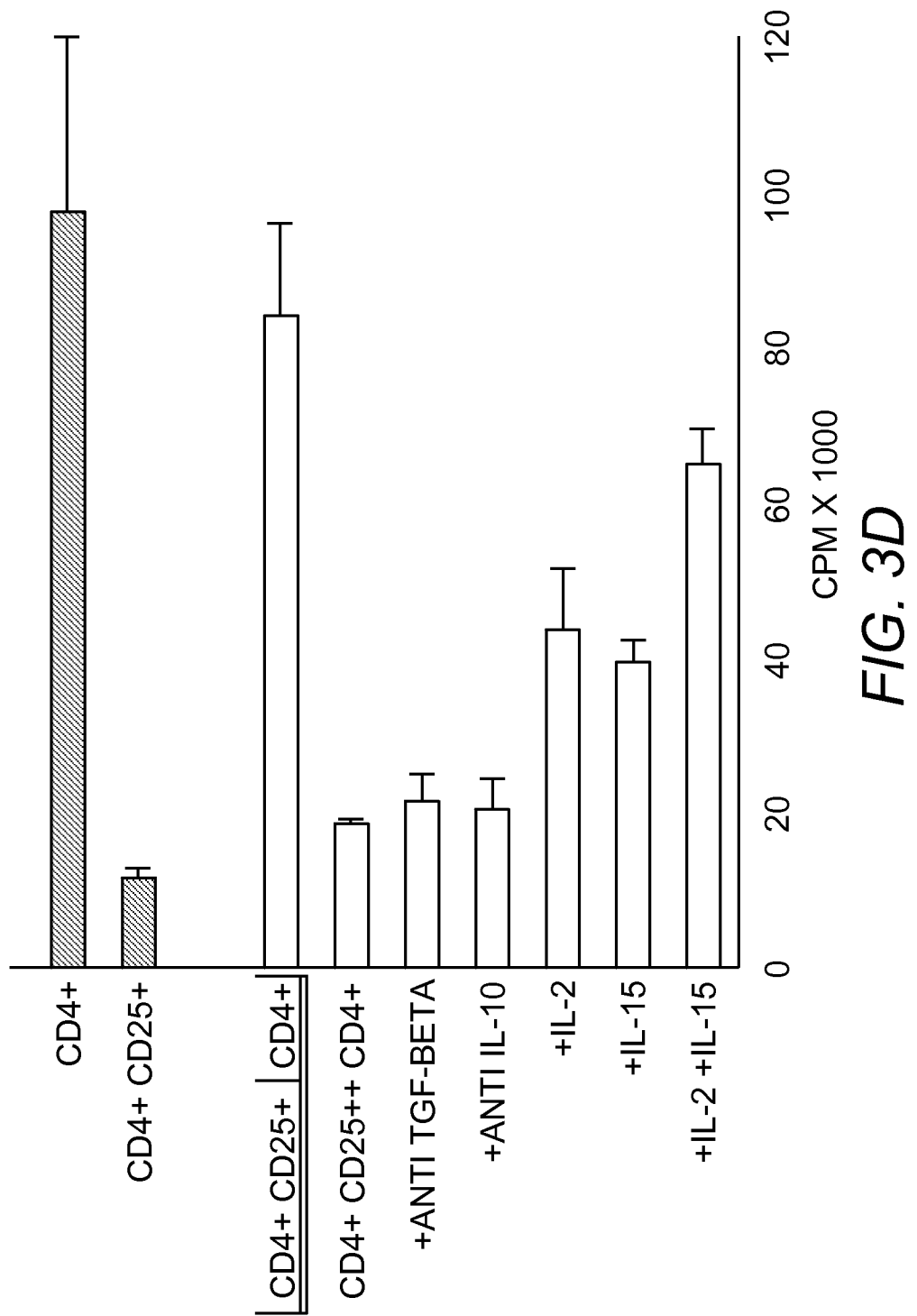
FIG. 3 shows that CD4+CD25+ T cells, if stimulated via the TCR, suppress the activation of CD4+ and CD8+ T cells in a cell contact- and dose-dependent manner.

Next, Transwell chamber experiments were performed to investigate, whether the regulatory function of the CD4+CD25+ T cells was mediated primarily by soluble factors or required cell-cell contact (FIG. 3D). As shown in FIG. 3D the CD4+CD25+ T cells suppress proliferation of whole CD4+ T cells almost completely in the presence of allogeneic DC. Separation of the two populations in Transwell chambers virtually abolished their suppressive effect. These observations suggested that direct cell contact is essential for the inhibitory capacity of CD4+CD25+ T cells, as the semipermeable membrane of Transwell chambers allows free passage of soluble factors, but excludes direct cell contact. The Transwell experiments also confirmed that consumption of IL-2 by CD4+CD25+ T cells was not the mechanism responsible for suppression.

Despite the obvious requirement for close interaction between regulatory and responding cells neither a targeting of the antigen-presenting DC or a role of soluble factors was excluded by the Transwell experiments. Therefore, a plate-bound anti-CD3 Ab (in combination with soluble anti CD28 Ab) was also employed as an antigen presenting cell-independent and polyclonal T cell stimulus. Whole CD4+ T cells alone showed strong proliferation upon this stimulation. As mentioned above (FIG. 2D) CD4+CD25+ T cells did not proliferate. In coculture of both populations, there was at least a 75% reduction at a 1:1 ratio compared to control (data not shown). These data suggested, that regulation does not primarily occur via modulation of APC function. Neutralizing antibodies to the cytokines IL-10 and TGF-β (critical for the suppressive activities of the so-called Tr1 and Th3, respectively (Groux, H. et al., Nature, 389:737-742 (1997); Fukaura, H. et al., J. Clin. Invest., 98:70-77 (1996)) did not abolish the regulatory activity of the CD4+CD25+ T cells demonstrating that these cytokines played no major suppressive role at least in the assays we looked at. The addition of IL-2 and/or IL-15 to cocultures at the high doses that promote the proliferation of CD4+CD25+ T cells (see FIG. 2D) reduced their inhibitory effects. The suppressive activity was, however, likely not abolished as the significant proliferation of the CD4+CD25+ T cells has to be taken into account when interpreting the data (FIG. 3D)

Example 4: CD4+CD25+ T Cells Predominantly Secrete IL-10

To analyze and compare the cytokine profiles freshly sorted CD4+CD25+ and CD4+CD25− T cells were activated with plate-bound anti CD3+anti CD28. Supernatants were then analyzed by ELISA, and RNA expression was studied by RNase protection assays. In addition, intracellular cytokine staining was performed to determine the percentage of cells releasing a certain cytokine. As shown in FIG. 4 $CD4^+CD25^-$ T cells predominantly secreted IFN-γ and IL-2, with little secretion of IL-10 and IL-4, resembling a Th1 like profile. $CD4^+CD25^+$ T cells on the other hand predominantly produced IL-10 and only low levels of IL-2, IL-4 and IFN-γ, resembling Tr1 cells. Comparison of both subpopulations at the RNA level revealed, that $CD25^+$ T cells express more IL-10, less IFN-γ and similar levels of IL-2 mRNA compared to $CD25^-$ T cells. IL-1 receptor antagonist (IL-1Ra) mRNA was found predominantly in $CD4^+CD25^+$ T cells, while significant IL-1β mRNA levels were only present in $CD4^+CD25^-$ T cells. TGF-β was expressed at similarly low levels in both cell types.

Example 5: Activated and Afterwards Fixated $CD4^+CD25^+$ T Cells Still Exhibit Regulatory Capacity $CD4^+CD25^-$ and $CD4^+CD25^+$ T cells were isolated from whole $CD4^+$ T cells from adult blood by MACS® sorting as described. $CD4^+CD25^+$ T cells were divided into three parts. One fraction was activated with 10 µg/ml platebound anti-CD3 and 10 µg/ml soluble anti-CD28 antibodies overnight. Next day this fraction and one part of the non activated $CD4^+CD25^+$ T cells were fixed with 2% formaldehyde for 1 hour. The third part was left untreated. Cells were washed three times.

Figure 5:
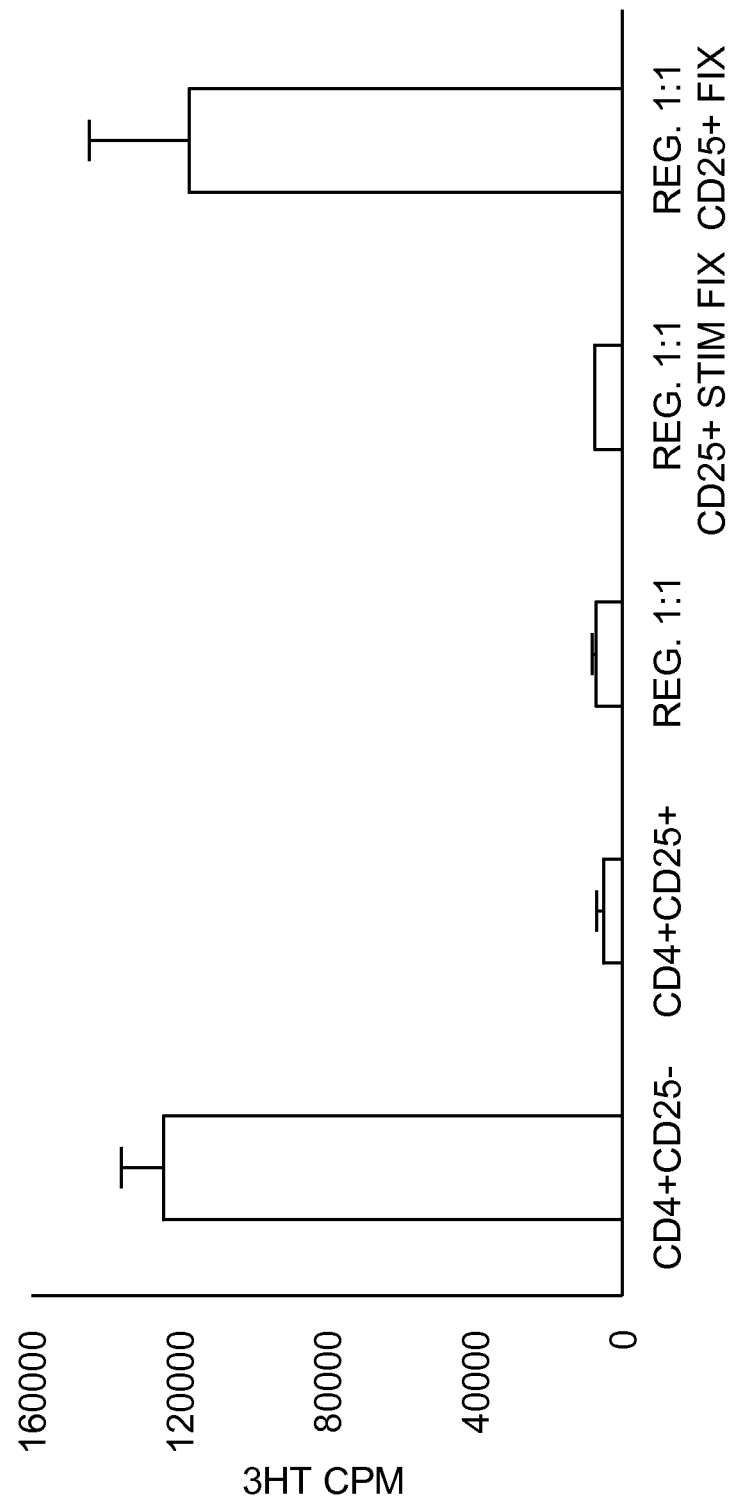
FIG. 5 shows that activated and fixated CD4+CD25+ cells still exhibit regulatory capacity.

Unfixed $CD4^+CD25^+$ and $CD4^+CD25^-$ T cells alone and $CD4^+CD25^+$ T cells of each fraction, mixed at a 1:1 ratio with $CD4^+CD25^-$ T cells, were activated with immobilized anti-CD3 and soluble anti-CD28. After 5 days proliferation was measured by [$^3$H]Tdr incorporation. A representative of 5 independent experiments is shown in FIG. 5 where the symbols represent the following:
$CD4^+CD25^-$ unfixed $CD4^+CD25^-$ cells
$CD4^+CD25^+$ unfixed $CD4^+CD25^+$ cells
Reg. 1:1 unfixed $CD4^+CD25^+$ and $CD4^+CD25^-$ T cells at a 1:1 ratio
Reg. 1:1
CD25+ stim fix activated fixed $CD4^+CD25^+$ T cells and unfixed $CD4^+CD25^-$ T cells at a 1:1 ratio
Reg. 1:1
CD25+ fix non activated fixed $CD4^+CD25^+$ T cells and unfixed $CD4^+CD25^-$ T cells at a 1:1 ratio

The invention claimed is:

1. A method for adoptive transfer therapy comprising:
 (a) isolating human $CD4^+CD25^+$ T cells from human blood to yield a population of isolated human $CD4^+CD25^+$ T cells;
 (b) binding anti-CTLA-4 antibodies to CTLA-4 expressed on the surface of unstimulated human regulatory $CD4^+CD25^+CTLA-4^+$ T cells preexisting within said population of isolated human $CD4^+CD25^+$ T cells to isolate from said population of isolated human $CD4^+CD25^+$ T cells a population of isolated human regulatory $CD4^+CD25^+CTLA-4^+$ T cells; and
 (c) injecting or infusing the isolated human regulatory $CD4^+CD25^+CTLA-4^+$ T cells into a human patient to treat in said human patient any immune reaction that is too strong and/or pathogenic, or to treat a transplantation reaction.

2. The method according to claim 1, wherein the human blood is human peripheral blood.

3. A method for adoptive transfer therapy comprising:
 (a) isolating human $CD4^+CD25^+$ T cells from human blood to yield a population of isolated human $CD4^+CD25^+$ T cells;
 (b) binding anti-CTLA-4 antibodies to CTLA-4 expressed on the surface of unstimulated human regulatory $CD4^+CD25^+CTLA-4^+$ T cells preexisting within said population of isolated human $CD4^+CD25^+$ T cells to isolate from said population of isolated human $CD4^+CD25^+$ T cells a population of isolated human regulatory $CD4^+CD25^+CTLA-4^+$ T cells;
 (c) expanding the isolated human regulatory $CD4^+CD25^+CTLA-4^+$ T cells to yield a population of expanded human regulatory $CD4^+CD25^+CTLA-4^+$ T cells; and
 (d) injecting or infusing the expanded human regulatory $CD4^+CD25^+CTLA-4^+$ T cells into a human patient to treat in said human patient any immune reaction that is too strong and/or pathogenic, or to treat a transplantation reaction.

4. The method of claim 3, wherein said human regulatory $CD4^+CD25^+CTLA-4^+$ T cells are expanded with a method comprising a step of stimulating the T cells with anti-CD3 and anti-CD28 antibodies.

5. The method of claim 4, wherein said method further comprises adding IL-2 and IL-15 to a culture of the T cells.

6. The method of claim 5, wherein IL-2 is used at a dose of 10 U/ml and IL-15 is used at a dose of 10 ng/ml.

7. The method of claim 3, wherein said human regulatory $CD4^+CD25^+CTLA-4^+$ T cells are expanded with a method comprising a step of stimulating the T cells with mature dendritic cells presenting an antigen in vitro.

8. The method of claim 7, wherein said antigen is a pathogen-derived antigen.

9. The method of claim 3, wherein said human regulatory $CD4^+CD25^+CTLA-4^+$ T cells are transfected with a T cell receptor of desired antigen specificity.

10. The method according to claim 3, wherein the human blood is human peripheral blood.

* * * * *